US010627460B2

(12) United States Patent
Alford et al.

(10) Patent No.: US 10,627,460 B2
(45) Date of Patent: Apr. 21, 2020

(54) SYSTEMS AND METHODS INCLUDING MULTI-MODE OPERATION OF OPTICALLY PUMPED MAGNETOMETER(S)

(71) Applicant: HI LLC, Los Angeles, CA (US)

(72) Inventors: Jamu Alford, Simi Valley, CA (US); Ricardo Jiménez-Martinez, North Hills, CA (US)

(73) Assignee: HI LLC, Los Angeles, CA (US)

( * ) Notice: Subject to any disclaimer, the term of this patent is extended or adjusted under 35 U.S.C. 154(b) by 0 days.

(21) Appl. No.: 16/213,980

(22) Filed: Dec. 7, 2018

(65) Prior Publication Data

US 2020/0072916 A1 Mar. 5, 2020

Related U.S. Application Data

(60) Provisional application No. 62/723,933, filed on Aug. 28, 2018.

(51) Int. Cl.
*G01R 33/26* (2006.01)
(52) U.S. Cl.
CPC .................... *G01R 33/26* (2013.01)
(58) Field of Classification Search
CPC .... G01R 33/26; G01R 33/032; G01R 33/282; G01R 33/24; G01R 33/3621
USPC ....................................................... 324/305
See application file for complete search history.

(56) References Cited

U.S. PATENT DOCUMENTS

| 4,951,674 A | 8/1990 | Zanakis et al. |
| 5,189,368 A | 2/1993 | Chase |
| 5,192,921 A | 3/1993 | Chantry et al. |
| 5,254,947 A | 10/1993 | Chaillout et al. |
| 5,309,095 A | 5/1994 | Ahonen et al. |
| 5,442,289 A | 8/1995 | Dilorio et al. |

(Continued)

FOREIGN PATENT DOCUMENTS

| CN | 104730484 | 6/2015 |
| CN | 106073751 | 11/2016 |

(Continued)

OTHER PUBLICATIONS

Fang, Jiancheng, and Jie Qin. "In situ triaxial magnetic field compensation for the spin-exchange-relaction-free atomic magnetometer." Review of Scientific Instruments 83.10 (2012): 103104. (Year: 2012).*

(Continued)

*Primary Examiner* — Christopher P McAndrew
(74) *Attorney, Agent, or Firm* — Lowe Graham Jones PLLC; Bruce E. Black

(57) ABSTRACT

A magnetic field measurement system that includes at least one magnetometer; at least one magnetic field generator; a processor coupled to the at least one magnetometer and the at least one magnetic field generator and configured to: measure an ambient background magnetic field using at least one of the at least one magnetometer in a first mode selected from a scalar mode or a vector mode; generate, in response to the measurement of the ambient background magnetic field, a compensation field using the at least one magnetic field generator; and measure a target magnetic field using at least one of the at least one magnetometer in a spin exchange relaxation free (SERF) mode which is different from the first mode.

25 Claims, 12 Drawing Sheets

(56) References Cited

U.S. PATENT DOCUMENTS

| | | |
|---|---|---|
| 5,444,372 A | 8/1995 | Wikswo, Jr. et al. |
| 5,471,985 A | 12/1995 | Warden |
| 5,506,200 A | 4/1996 | Hirschkoff et al. |
| 5,526,811 A | 6/1996 | Lypchuk |
| 5,713,354 A | 2/1998 | Warden |
| 6,144,872 A | 11/2000 | Graetz |
| 6,339,328 B1 | 1/2002 | Keene et al. |
| 6,472,869 B1 | 10/2002 | Upschulte et al. |
| 6,665,553 B2 | 12/2003 | Kandori et al. |
| 6,806,784 B2 | 10/2004 | Hollberg et al. |
| 6,831,522 B2 | 12/2004 | Kitching et al. |
| 7,038,450 B2 | 5/2006 | Romalis et al. |
| 7,102,451 B2 | 9/2006 | Happer et al. |
| 7,145,333 B2 | 12/2006 | Romalis et al. |
| 7,521,928 B2 | 4/2009 | Romalis et al. |
| 7,656,154 B2 | 2/2010 | Kawabata et al. |
| 7,826,065 B1 | 11/2010 | Okandan et al. |
| 7,872,473 B2 | 1/2011 | Kitching et al. |
| 7,994,783 B2 | 8/2011 | Ledbetter et al. |
| 8,054,074 B2 | 11/2011 | Lohihara et al. |
| 8,212,556 B1 | 7/2012 | Schwindt et al. |
| 8,334,690 B2 | 12/2012 | Kitching et al. |
| 8,373,413 B2 | 2/2013 | Sugioka |
| 8,405,389 B2 | 3/2013 | Sugioka et al. |
| 8,587,304 B2 | 11/2013 | Budker et al. |
| 8,836,327 B2 | 9/2014 | French et al. |
| 8,906,470 B2 | 12/2014 | Overstolz et al. |
| 8,941,377 B2 | 1/2015 | Mizutani et al. |
| 9,095,266 B1 | 8/2015 | Fu |
| 9,116,201 B2 | 8/2015 | Shah et al. |
| 9,140,590 B2 | 9/2015 | Waters et al. |
| 9,140,657 B2 | 9/2015 | Ledbetter et al. |
| 9,169,974 B2 | 10/2015 | Parsa et al. |
| 9,244,137 B2 | 1/2016 | Kobayashi et al. |
| 9,291,508 B1 | 3/2016 | Biedermann et al. |
| 9,343,447 B2 | 3/2016 | Parsa et al. |
| 9,366,735 B2 | 6/2016 | Kawabata et al. |
| 9,383,419 B2 | 7/2016 | Mizutani et al. |
| 9,395,425 B2 | 7/2016 | Diamond et al. |
| 9,417,293 B2 | 8/2016 | Schaffer et al. |
| 9,429,918 B2 | 8/2016 | Parsa et al. |
| 9,568,565 B2 | 2/2017 | Parsa et al. |
| 9,575,144 B2 | 2/2017 | Kornack et al. |
| 9,601,225 B2 | 3/2017 | Parsa et al. |
| 9,638,768 B2 | 5/2017 | Foley et al. |
| 9,639,062 B2 | 5/2017 | Dyer et al. |
| 9,677,905 B2 | 6/2017 | Waters et al. |
| 9,726,626 B2 | 8/2017 | Smith et al. |
| 9,726,733 B2 | 8/2017 | Smith et al. |
| 9,791,536 B1 | 10/2017 | Alem et al. |
| 9,829,544 B2 | 11/2017 | Bulatowicz |
| 9,846,054 B2 | 12/2017 | Waters et al. |
| 9,851,418 B2 | 12/2017 | Wolf et al. |
| 9,869,731 B1* | 1/2018 | Hovde .................. G01R 33/26 |
| 9,915,711 B2 | 3/2018 | Kornack et al. |
| 9,927,501 B2 | 3/2018 | Kim et al. |
| 9,948,314 B2 | 4/2018 | Dyer et al. |
| 9,964,609 B2 | 5/2018 | Ichihara et al. |
| 9,964,610 B2 | 5/2018 | Shah et al. |
| 9,970,999 B2 | 5/2018 | Larsen et al. |
| 10,024,929 B2 | 7/2018 | Parsa et al. |
| 10,088,535 B1 | 10/2018 | Shah |
| 10,162,016 B2 | 12/2018 | Gabrys et al. |
| 2004/0232912 A1 | 11/2004 | Tsukamoto et al. |
| 2005/0007118 A1 | 1/2005 | Kitching et al. |
| 2005/0046851 A1 | 3/2005 | Riley, Jr. et al. |
| 2005/0206377 A1 | 9/2005 | Romalis et al. |
| 2007/0120563 A1* | 5/2007 | Kawabata .......... G01R 33/0354 324/244.1 |
| 2007/0167723 A1 | 7/2007 | Park et al. |
| 2007/0205767 A1* | 9/2007 | Xu ........................ G01R 33/26 324/304 |
| 2009/0079426 A1 | 3/2009 | Anderson |
| 2010/0219820 A1 | 9/2010 | Skidmore et al. |
| 2011/0062956 A1 | 3/2011 | Edelstein et al. |
| 2012/0112749 A1 | 5/2012 | Budker et al. |
| 2013/0082700 A1 | 4/2013 | Mizutani et al. |
| 2013/0082701 A1 | 4/2013 | Mizutani et al. |
| 2014/0354275 A1 | 12/2014 | Shang et al. |
| 2015/0022200 A1 | 1/2015 | Ichihara et al. |
| 2015/0054504 A1 | 2/2015 | Ichihara et al. |
| 2015/0378316 A1 | 12/2015 | Parsa et al. |
| 2016/0061913 A1 | 3/2016 | Kobayashi et al. |
| 2016/0116553 A1* | 4/2016 | Kim ..................... G01R 33/032 324/305 |
| 2016/0223627 A1 | 8/2016 | Shah et al. |
| 2016/0313417 A1* | 10/2016 | Kawabata ............. G01R 33/26 |
| 2017/0023653 A1 | 1/2017 | Kobayashi et al. |
| 2017/0023654 A1 | 1/2017 | Kobayashi et al. |
| 2017/0199138 A1 | 7/2017 | Parsa et al. |
| 2017/0261564 A1 | 9/2017 | Gabrys et al. |
| 2017/0331485 A1 | 11/2017 | Gobet et al. |
| 2017/0343617 A1 | 11/2017 | Manickam et al. |
| 2017/0343695 A1 | 11/2017 | Stetson et al. |
| 2018/0003777 A1 | 1/2018 | Sorenson et al. |
| 2018/0038921 A1 | 2/2018 | Parsa et al. |
| 2018/0100749 A1 | 4/2018 | Waters et al. |
| 2018/0128885 A1 | 5/2018 | Parse et al. |
| 2018/0156875 A1 | 6/2018 | Herbsommer et al. |
| 2018/0219353 A1 | 8/2018 | Shah |
| 2018/0238974 A1 | 8/2018 | Shah et al. |
| 2018/0313908 A1 | 11/2018 | Knappe et al. |

FOREIGN PATENT DOCUMENTS

| | | |
|---|---|---|
| CN | 107562188 | 1/2018 |
| EP | 2738627 A3 | 6/2014 |
| EP | 2380029 B1 | 10/2015 |
| EP | 3037836 B1 | 9/2017 |
| JP | 2012100839 | 5/2012 |
| JP | 2016109665 | 6/2016 |
| JP | 2018004462 | 1/2018 |
| WO | 2005/081794 | 9/2005 |
| WO | 2014/031985 | 2/2014 |
| WO | 2017/095998 | 6/2017 |

OTHER PUBLICATIONS

Seltzer, S.J. and Romalis, M.V., 2004. Unshielded three-axis vector operation of a spin-exchange-relaxation-free atomic magnetometer. Applied physics letters, 85(20), pp. 4804-4806. (Year: 2004).*

Fang, Jiancheng, and Jie Qin. "In situ triaxial magnetic field compensation for the spin-exchange-relaxation-free atomic magnetometer." Review of Scientific Instruments 83.10 (2012): 103104. (Year: 2012).*

Huang, Haichao, et al. "Single-beam three-axis atomic magnetometer." Applied Physics Letters 109.6 (2016): 062404. (Year: 2016).*

Allred, J. C., Lyman, R. N., Kornack, T. W., & Romalis, M. V. (2002). High-sensitivity atomic magnetometer unaffected by spin-exchange relaxation. Physical review letters, 89(13), 130801.

Balabas et al. Polarized alkali vapor with minute-long transverse spin-relaxation time, Phys. Rev. Lett. 105, 070801—Published Aug. 12, 2010.

Barbieri, F., Trauchessec, V., Caruso, L., Trejo-Rosillo, J., Telenczuk, B., Paul, E., . . . & Ouanounou, G. (2016). Local recording of biological magnetic fields using Giant Magneto Resistance-based micro-probes. Scientific reports, 6, 39330.

Dmitry Budker and Michael Romalis, "Optical Magnetometry," Nature Physics, 2008, https://arxiv.org/abs/physics/0611246v1.

Anthony P. Colombo, Tony R. Carter, Amir Boma, Yuan-Yu Jau, Cort N. Johnson, Amber L. Dagel, and Peter D. D. Schwindt, "Four-channel optically pumped atomic magnetometer for magnetoencephalography," Opt. Express 24, 15403-15416 (2016).

Dang, H.B. & Maloof, A.C. & Romalis, Michael. (2009). Ultra-high sensitivity magnetic field and magnetization measurements with an atomic magnetometer. Applied Physics Letters. 97. 10.1063/1. 3491215.

Donley, E.A. & Hodby, E & Hollberg, L & Kitching, J. (2007). Demonstration of high-performance compact magnetic shields for chip-scale atomic devices, The Review of scientific instruments. 78. 083102.

(56) References Cited

OTHER PUBLICATIONS

Hämäläinen, Matti & Han, Riitta & Ilmoniemi, Risto J. & Knuutila, Jukka & Lounasmaa, Olli V. Apr. 1993. Magnetoencephalograph—theory, instrumentation, and applications to noninvasive studies of the working human brain. Reveiw of Modern Physics. vol. 65, Issue 2. 413-497.

Hunter, D. and Piccolomo, S. and Pritchard, J. D. and Brockie, N. L. and Dyer, T. E. and Riis, E, (2018) Free-induction-decay magnetometer based on a microfabricated Cs vapor cell. Physical Review Applied (10).ISSN 2331-7019.

Jiménez-Martinez, R., Griffith, W. C., Wang, Y. J., Knappe, S., Kitching, J., Smith, K., & Prouty, M. D. (2010). Sensitivity comparison of Mx and frequency-modulated bell—bloom Cs magnetometers in a microfabricated cell. IEEE Transactions on Instrumentation and Measurement, 59(2), 372-378.

Kiwoong Kim, Samo Begus, Hui Xia, Seung-Kyun Lee, Vojko Jazbinsek, Zvonko Trontelj, Michael V. Romalis, Multi-channel atomic magnetometer for magnetoencephalography: A configuration study. NeuroImage 89 (2014) 143-151 http://physics.princeton.edu/romalis/papers/Kim_2014.pdf.

Knappe, Svenja & Sander, Tilmann & Trahms, Lutz. (2012). Optically-Pumped Magnetometers for MEG. Magnetoencephalography: From Signals to Dynamic Cortical Networks. 993-999. 10.1007/978-3-642-33045-2_49.

Kominis, I.K., Kornack, T.W., Allred, J.C. and Romalis, M.V., 2003. A subfemtotesla multichannel atomic magnetometer. Nature, 422(6932), p. 596.

Korth, H., K. Strohbehn, F. Tejada, A. G. Andreou, J. Kitching, S. Knappe, S. J. Lehtonen, S. M. London, and M. Kafel (2016), Miniature atomic scalar magnetometer for space based on the rubidium isotope 87Rb, J. Geophys. Res. Space Physics, 121, 7870-7880, doi:10,1002/2016JA022389.

Lenz, J. and Edelstein, S., 2006. Magnetic sensors and their applications. IEEE Sensors journal, 6(3), pp. 631-649.

Li, S & Vachaspati, Pranjal & Sheng, Dehong & Dural, Nezih & Romalis, Michael. (2011). Optical rotation in excess of 100 rad generated by Rb vapor in a multipass cell. Phys. Rev. A. 84. 10.1103/PhysRevA.84.061403.

Maze, J. R., Stanwix, P. L., Hodges, J. S., Hong, S., Taylor, J. M., Cappellaro, P., . . . & Yacoby, A. (2008). Nanoscale magnetic sensing with an individual electronic spin in diamond. Nature, 455(7213), 644.

Sander TH, Preusser J, Mhaskar R, Kitching J, Trahms L, Knappe S. Magnetoencephalography with a chip-scale atomic magnetometer. Biomed Opt Express. 2012;3(5):981-90.

J. Seltzer, S & Romalis, Michael. (2010). High-temperature alkali vapor cells with antirelaxation surface coatings. Journal of Applied Physics. 106, 114905-114905. 10.1063/1.3236649.

Seltzer, S. J., and Romalis. M.V., "Unshielded three-axis vector operation of a spin-exchange-relaxation-free atomic magnetometer." Applied physics letters 85.20 (2004): 4804-4806.

Sheng, Dong & R. Perry, Abigail & Krzyzewski, Sean & Geller, Shawn & Kitching, John & Knappe, Svenja. (2017). A microfabricated optically-pumped magnetic gradiometer. Applied Physics Letters. 110. 10.1063/1.4974349.

Sheng, Dehong & Li, S & Dural, Nezih & Romalis, Michael. (2013). Subfemtotesla Scalar Atomic Magnetometry Using Multipass Cells. Physical review letters. 110. 160802. 10.1103/PhysRevLett.110.160802.

Volkmar Schultze et al. An Optically Pumped Magnetometer Working in the Light-Shift Dispersed Mz Mode, Sensors 2017, 17, 561; doi:10.3390/s17030561.

Fang, J. and Qin, J., 2012. In situ triaxial magnetic field compensation for the spin-exchange-relaxation-free atomic magnetometer. Review of Scientific Instruments, 83(10), p. 103104.

Joon Lee, Hyun & Shim, Jeong & Moon, Han Seb & Kim, Kiwoong. (2014). Flat-response spin-exchange relaxation free atomic magnetometer under negative feedback. Optics Express. 22. 10,1364/OE.22.019887.

Griffith, Clark & Jimenez-Martinez, Ricardo & Shah, Vishal & Knappe, Svenja & Kitching, John. (2009). Miniature atomic magnetometer integrated with flux concentrators. Applied Physics Letters—Appl Phys Lett. 94. 10.1063/1.3056152.

Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.2885711.

Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-018-20352-x.

Kim, Young Jin & Savukov, I. (2016). Ultra-sensitive Magnetic Microscopy with an Optically Pumped Magnetometer, Scientific Reports. 6. 24773. 10.1038/srep24773.

Navau, Carles & Prat-Camps, Jordi & Sanchez, Alvaro. (2012). Magnetic Energy Harvesting and Concentration at a Distance by Transformation Optics. Physical review letters. 109. 263903. 10.1103/PhysRevLett.109.263903.

Orang Alem, Rahul Mhaskar, Ricardo Jiménez-Martinez, Dong Sheng, John LeBlanc, Lutz Trahms, Tilmann Sander, John Kitching, and Svenja Knappe, "Magnetic field imaging with microfabricated optically-pumped magnetometers," Opt. Express 25, 7849-7858 (2017).

Slocum et al., Self-Calibrating Vector Magnetometer for Space, https://esto.nasa.gov/conferences/estc-2002/Papers/B3P4(Slocum).pdf.

Dupont-Roc, J & Haroche, S & Cohen-Tannoudji, C. (1969). Detection of very weak magnetic fields (10-9gauss) by 87Rb zero-field level crossing resonances. Physics Letters A-PHYS LETT A. 28. 638-639. 10.1016/0375-9601(69)90480-0.

J. A. Neuman, P. Wang, and A. Gallagher, Robust high-temperature sapphire cell for metal vapors, Review of Scientific Instruments, vol. 66, Issue 4, Apr. 1995, pp. 3021-3023.

Borna, Amir, et al. "A 20-channel magnetoencephalography system based on optically pumped magnetometers." Physics in Medicine & Biology 62.23 (2017): 8909.

R. E. Slocum & L. J. Ryan, Design and operation of the minature vector laser magnetometer, Nasa Earth Science Technology Conference 2003.

Schoenmaker, Jeroen & R Pirota, K & Teixeira, Julio. (2013). Magnetic flux amplification by Lenz lenses. The Review of scientific instruments. 84. 085120. 10.1063/1.4819234.

Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic modulator detection in the optically pumped magnetometer. Applied Optics. 56. 5927. 10.1364/AO.56.005927.

Lorenz, V. O., Dai, X., Green, H., Asnicar, T, R., & Cundiff, S. T. (2008). High-density, high-temperature alkali vapor cell. Review of Scientific Instruments, 79(12), 4 pages.

F. Jackson Kimball, D & Dudley, J & Li, Y & Thulasi, Swecha & Pustelny, Szymon & Budker, Dmitry & Zolotorev, Max. (2016). Magnetic shielding and exotic spin-dependent interactions. Physical Review D. 94. 10.1103/PhysRevD.94.082005.

Scott Jeffrey Seltzer: "Developments in alkali-metal atomic magnetometry", Nov. 1, 2008 (Nov. 1, 2008), XP055616618, ISBN: 978-0-549-93355-7 Retrieved from the Internet: URL:http://physics.princeton.edu/atomic/romalis/papers/Seltzer%20Thesis.pdf [retrieved on Jun. 29, 2019] pp. 143-159.

Haifeng Dong et al: "Atomic-Signal-Based Zero-Field Finding Technique for Unshielded Atomic Vector Magnetometer", IEEE Sensors Journal, IEEE Service Center, New York, NY, US, vol. 13, No. 1, Jan. 1, 2013 (Jan. 1, 2013), pp. 186-189.

International Search Report and Written Opinion for PCT Application No. PCT/US2019/033332 dated Sep. 12, 2019

Masuda, Y & Ino, T & Skoy, Vadim & Jones, G.L. (2005). 3He polarization via optical pumping in a birefringent cell. Applied Physics Letters. 87, 10.1063/1.2008370.

(56) References Cited

OTHER PUBLICATIONS

A.B. Baranga et al., An atomic magnetometer for brain activity imaging, Real Time Conference 2005. 14th IEEE-NPSS. pp. 417-418.
Larry J. Ryan, Robert E. Slocum, and Robert B. Steves, Miniature Vector Laser Magnetometer Measurements of Earth's Field, May 10, 2004, 4 pgs.

* cited by examiner

SYSTEMS AND METHODS INCLUDING MULTI-MODE OPERATION OF OPTICALLY PUMPED MAGNETOMETER(S)

CROSS-REFERENCE TO RELATED APPLICATIONS

This application claims the benefit of U.S. Provisional Patent Application Ser. No. 62/723,933, filed Aug. 28, 2018, which is incorporated herein by reference in its entirety.

FIELD

The present disclosure is directed to the area of magnetic field measurement systems using one or more optically pumped magnetometers. The present disclosure is also directed to magnetic field measurement systems and methods that include operation in scalar/vector and spin exchange relaxation free (SERF) modes using one or more magnetometers.

BACKGROUND

In the nervous system, neurons propagate signals via action potentials. These are brief electric currents which flow down the length of a neuron causing chemical transmitters to be released at a synapse. The time-varying electrical current within the neuron generates a magnetic field, which propagates through the human body and can be measured using either a Superconductive Quantum Interference Device (SQUID) or an Optically Pumped Magnetometer (OPM). In this disclosure the OPM is primarily considered because the SQUID requires cryogenic cooling, which may make it prohibitively costly for users and too large to be wearable by a user. In addition to OPMs and SQUIDs, other magnetic sensing technologies for detection of magnetic fields from the brain include and magnetoresistance.

Optical magnetometry can include the use of optical methods to measure a magnetic field with very high accuracy—on the order of $1 \times 10^{-15}$ Tesla. Of particular interest for their high-sensitivity, an optically pumped magnetometer (OPM) can be used in optical magnetometry to measure weak magnetic fields. In at least some embodiments, the OPM has an alkali vapor gas cell that contains alkali metal atoms in a combination of gas, liquid, or solid states (depending on temperature). The gas cell may contain a quenching gas, buffer gas, or specialized antirelaxation coatings or any combination thereof. The size of the gas cells can vary from a fraction of a millimeter up to several centimeters.

BRIEF SUMMARY

One embodiment is a magnetic field measurement system that includes at least one magnetometer; at least one magnetic field generator; a processor coupled to the at least one magnetometer and the at least one magnetic field generator and configured to: i) measure an ambient background magnetic field using at least one of the at least one magnetometer in a first mode selected from a scalar mode or a vector mode; ii) generate, in response to the measurement of the ambient background magnetic field, a compensation field using the at least one magnetic field generator; iii) measure a target magnetic field using at least one of the at least one magnetometer in a spin exchange relaxation free (SERF) mode which is different from the first mode and iv) determine when the at least one of the at least one magnetometer is not operating in SERF mode and automatically perform steps i) and ii) again. For example, the first mode can be a scalar mode or a non-SERF vector mode.

In at least some embodiments, the at least one magnetometer includes a first magnetometer configured to operate in both the first mode and the SERF mode and the processor is configured to operate the first magnetometer in both the first mode and the SERF mode. In at least some embodiments, the at least one magnetometer includes a first magnetometer configured to operate in the first mode and a second magnetometer configured to operate in the SERF mode. In at least some embodiments, each of the at least one magnetometer includes a vapor cell and the first and second magnetometers share the same vapor cell.

In at least some embodiments, the processor is further configured to: measure the ambient background magnetic field, reduced by compensation field, using at least one of the at least one magnetometer in the SERF mode; and update, in response to the measurement of the ambient background magnetic field reduced by compensation field, the compensation field using the at least one magnetic field generator. In at least some embodiments, measuring the ambient background magnetic field includes, for each of two or three orthogonal axes: applying a first magnetic field along the axis; sweeping a frequency of the first magnetic field; measuring responses by the at least one of the at least one magnetometer in the first mode during the sweeping; and determining a vector component of the ambient background magnetic field along the axis by observing a maximum or minimum in the responses or fitting the responses to a Lorentzian function.

In at least some embodiments, measuring the ambient background magnetic field includes applying a first magnetic field along a first axis; sweeping a frequency of the first magnetic field; measuring responses by the at least one of the at least one magnetometer in the first mode during the sweeping; and determining a magnitude of the ambient background magnetic field along the axis by observing a maximum or minimum in the responses or fitting the responses to a Lorentzian function. In at least some embodiments, measuring the ambient background magnetic field further includes, for each of two or three orthogonal axes: applying a first magnetic field along the axis; modulating the first magnetic field; measuring responses by the at least one of the at least one magnetometer in a vector mode during the modulation; and determining a vector component of the ambient background magnetic field along the axis by observing the responses to the modulated first magnetic field.

In at least some embodiments, the magnetic field measurement system further includes at least one local oscillator coupled to the at least one magnetometer; and at least one lock-in amplifier, each of the at least one lock-in amplifier coupled to a one of the at least one local oscillator and at least one of the at least one magnetometer.

Another embodiment is a magnetic field measurement system that includes at least one first magnetometer configured for operation in a first mode selected from a scalar mode or a vector mode; at least one second magnetometer configured for operation in a spin exchange relaxation free (SERF) mode which is different from the first mode; at least one magnetic field generator; and a processor coupled to the at least one first magnetometer, the at least one second magnetometer, and the at least one magnetic field generator and configured to: measure an ambient background magnetic field using at least one of the at least one first magnetometer; and generate of a compensation field by the at least one magnetic field generator based on the measurement from the at least one first magnetometer. For example, the first mode can be a scalar mode or a non-SERF vector mode.

In at least some embodiments, each of the at least one first magnetometer and each of the at least one second magnetometer includes a vapor cell and at least one of the at least one first magnetometer and at least one of the at least one second magnetometers share the same vapor cell.

In at least some embodiments, the processor is further configured to: measure the ambient background magnetic field, reduced by compensation field, using at least one of the at least one second magnetometer; and update, in response to the measurement of the ambient background magnetic field reduced by compensation field, the compensation field using the at least one magnetic field generator. In at least some embodiments, measuring the ambient background magnetic field includes, for each of two or three orthogonal axes: applying a first magnetic field along the axis; sweeping a frequency of the first magnetic field; measuring responses by the at least one of the at least one first magnetometer in the first mode during the sweeping; and determining a vector component of the ambient background magnetic field along the axis by observing a maximum or minimum in the responses or fitting the responses to a Lorentzian function.

In at least some embodiments, measuring the ambient background magnetic field includes: applying a first magnetic field along a first axis; sweeping a frequency of the first magnetic field; measuring responses by the at least one of the at least one first magnetometer in the first mode during the sweeping; and determining a magnitude of the ambient background magnetic field along the axis by observing a maximum or minimum in the responses or fitting the responses to a Lorentzian function. In at least some embodiments, measuring the ambient background magnetic field further includes, for each of two or three orthogonal axes: applying a first magnetic field along the axis; modulating the first magnetic field; measuring responses by the at least one of the at least one first or second magnetometer in a vector mode during the modulation; and determining a vector component of the ambient background magnetic field along the axis by observing the responses to the modulated first magnetic field.

In at least some embodiments, the magnetic field measurement system further includes at least one local oscillator coupled to at least one of the at least one first magnetometer; and at least one lock-in amplifier, each of the at least one lock-in amplifier coupled to a one of the at least one local oscillator and at least one of the at least one first magnetometer.

A further embodiment is a non-transitory processor readable storage media that includes instructions for operating a magnetic field measurement system including at least one magnetometer and at least one magnetic field generator, wherein execution of the instructions by one or more processors cause the one or more processors to perform actions, including: i) measuring an ambient background magnetic field using at least one of the at least one magnetometer operating in a first mode selected from a scalar mode or a vector mode; ii) generating, in response to the measurement of the ambient background magnetic field, a compensation field using the at least one magnetic field generator; iii) measuring a target magnetic field using at least one of the at least one magnetometer operating in a spin exchange relaxation free (SERF) mode which is different from the first mode and iv) determining when the at least one of the at least one magnetometer is not operating in SERF mode and automatically performing steps i) and ii) again. For example, the first mode can be a scalar mode or a non-SERF vector mode.

In at least some embodiments, measuring the ambient background magnetic field using the at least one of the at least one magnetometer operating in a first mode and measuring the target magnetic field using at least one of the at least one magnetometer operating in the spin exchange relaxation free (SERF) mode include measuring the ambient background magnetic field and measuring the target magnetic field using the same magnetometer. In at least some embodiments, the actions further include: measuring the ambient background magnetic field, reduced by compensation field, using at least one of the at least one magnetometer in the SERF mode; and updating, in response to the measurement of the ambient background magnetic field reduced by compensation field, the compensation field using the at least one magnetic field generator.

In at least some embodiments, measuring the ambient background magnetic field includes, for each of two or three orthogonal axes: applying a first magnetic field along the axis; sweeping a frequency of the first magnetic field; measuring responses by the at least one of the at least one magnetometer in the first mode during the sweeping; and determining a vector component of the ambient background magnetic field along the axis by observing a maximum or minimum in the responses or fitting the responses to a Lorentzian function.

In at least some embodiments, measuring the ambient background magnetic field includes: applying a first magnetic field along a first axis; sweeping a frequency of the first magnetic field; measuring responses by the at least one of the at least one magnetometer in the first mode during the sweeping; and determining a magnitude of the ambient background magnetic field along the axis by observing a maximum or minimum in the responses or fitting the responses to a Lorentzian function. In at least some embodiments, measuring the ambient background magnetic field further includes, for each of two or three orthogonal axes: applying a first magnetic field along the axis; modulating the first magnetic field; measuring responses by the at least one of the at least one magnetometer in a vector mode during the modulation; and determining a vector component of the ambient background magnetic field along the axis by observing the responses to the modulated first magnetic field.

Yet another embodiment is a method of operating a magnetic field measurement system that includes at least one magnetometer and at least one magnetic field generator. The method includes i) measuring an ambient background magnetic field using at least one of the at least one magnetometer operating in a first mode selected from a scalar mode or a vector mode; ii) generating, in response to the measurement of the ambient background magnetic field, a compensation field using the at least one magnetic field generator; iii) measuring a target magnetic field using at least one of the at least one magnetometer operating in a spin exchange relaxation free (SERF) mode which is different from the first mode; and iv) determining when the at least one of the at least one magnetometer is not operating in SERF mode and performing steps i) and ii) again. For example, the first mode can be a scalar mode or a non-SERF vector mode.

In at least some embodiments, measuring the ambient background magnetic field using the at least one of the at least one magnetometer operating in the first mode and measuring the target magnetic field using at least one of the at least one magnetometer operating in the spin exchange relaxation free (SERF) mode include measuring the ambient background magnetic field and measuring the target magnetic field using the same magnetometer.

In at least some embodiments, measuring the ambient background magnetic field using the at least one of the at least one magnetometer operating in a first mode includes measuring the ambient background magnetic field using a first magnetometer of the at least one magnetometer, the first magnetometer operating in the first mode; and measuring the target magnetic field using at least one of the at least one magnetometer operating in the spin exchange relaxation free (SERF) mode include measuring the target magnetic field using a second magnetometer of the at least one magnetometer, the first magnetometer operating in the SERF mode. In at least some embodiments, each of the at least one magnetometer includes a vapor cell and the first and second magnetometers share the same vapor cell.

In at least some embodiments, the method further includes measuring the ambient background magnetic field, reduced by compensation field, using at least one of the at least one magnetometer in the SERF mode; and updating, in response to the measurement of the ambient background magnetic field reduced by compensation field, the compensation field using the at least one magnetic field generator. In at least some embodiments, measuring the ambient background magnetic field includes, for each of two or three orthogonal axes: applying a first magnetic field along the axis; sweeping a frequency of the first magnetic field; measuring responses by the at least one of the at least one magnetometer in the first mode during the sweeping; and determining a vector component of the ambient background magnetic field along the axis by observing a maximum or minimum in the responses or fitting the responses to a Lorentzian function.

In at least some embodiments, measuring the ambient background magnetic field includes: applying a first magnetic field along a first axis; sweeping a frequency of the first magnetic field; measuring responses by the at least one of the at least one magnetometer in the first mode during the sweeping; and determining a magnitude of the ambient background magnetic field along the axis by observing a maximum or minimum in the responses or fitting the responses to a Lorentzian function. In at least some embodiments, measuring the ambient background magnetic field further includes, for each of two or three orthogonal axes: applying a first magnetic field along the axis; modulating the first magnetic field; measuring responses by the at least one of the at least one magnetometer in a vector mode during the modulation; and determining a vector component of the ambient background magnetic field along the axis by observing the responses to the modulated first magnetic field.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1A:
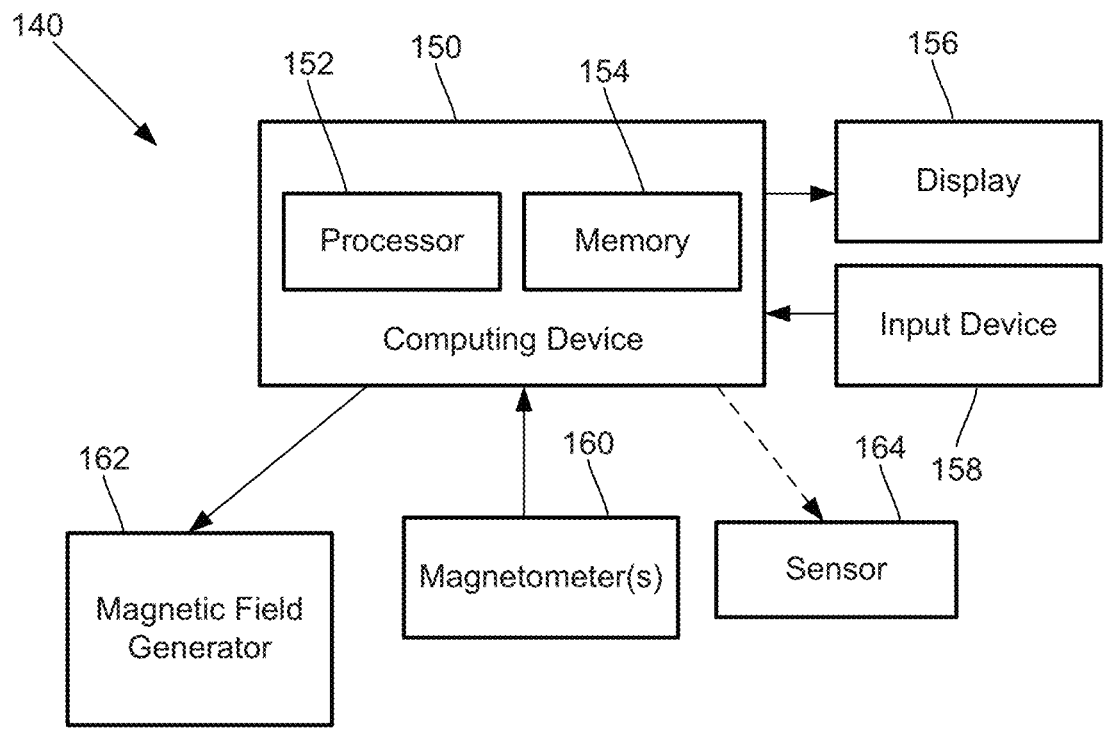
FIG. 1A is a schematic block diagram of one embodiment of a magnetic field measurement system, according to the invention.

The present disclosure is directed to the area of magnetic field measurement systems using one or more optically pumped magnetometers. The present disclosure is also directed to magnetic field measurement systems and methods that include operation in scalar/vector and spin exchange relaxation free (SERF) modes using one or more magnetometers.

Herein the terms "ambient background magnetic field" and "background magnetic field" are interchangeable and used to identify the magnetic field or fields associated with sources other than the magnetic field measurement system and the biological source(s) (for example, neural signals from a user's brain) or other source(s) of interest. The terms can include, for example, the Earth's magnetic field, as well as magnetic fields from magnets, electromagnets, electrical devices, and other signal or field generators in the environment, except for the magnetic field generator(s) that are part of the magnetic field measurement system.

The terms "gas cell", "vapor cell", and "vapor gas cell" are used interchangeably herein. Below, a gas cell containing alkali metal vapor is described, but it will be recognized that other gas cells can contain different gases or vapors for operation.

An optically pumped magnetometer (OPM) is a basic component used in optical magnetometry to measure magnetic fields. While there are many types of OPMs, in general magnetometers operate in two modalities: vector mode and scalar mode. In vector mode, the OPM can measure one, two, or all three vector components of the magnetic field; while in scalar mode the OPM can measure the total magnitude of the magnetic field.

Vector mode magnetometers measure a specific component of the magnetic field, such as the radial and tangential components of magnetic fields with respect the scalp of the human head. Vector mode OPMs often operate at zero-fields and may utilize a spin exchange relaxation free (SERF) mode to reach femto-Tesla sensitivities. A SERF mode OPM is one example of a vector mode OPM, but other vector mode OPMs can be used at higher magnetic fields. These SERF mode magnetometers can have high sensitivity but in general cannot function in the presence of magnetic fields higher than the linewidth of the magnetic resonance of the atoms of about 10 nT, which is much smaller than the magnetic field strength generated by the Earth. As a result, conventional SERF mode magnetometers often operate inside magnetically shielded rooms that isolate the sensor from ambient magnetic fields including Earth's.

Magnetometers operating in the scalar mode can measure the total magnitude of the magnetic field. (Magnetometers in the vector mode can also be used for magnitude measurements.) Scalar mode OPMs often have lower sensitivity than SERF mode OPMs. However, scalar mode OPMs can operate in unshielded environments up to and including the Earth field, which is about 50 µT. Furthermore, as the magnetic readings from scalar mode OPMs do not suffer from long-term drifts and bias they are frequently used to calibrate other magnetic sensors.

In optically pumped magnetometers (OPMs), which are based on the precession of atomic spins, another classification is based on the strength of the effective magnetic field experienced by the atoms in the gas cell, where two regimes are identified: zero-field mode and finite-field mode. Finite-field OPMs operate in a regime where the magnitude of the field experienced by the atoms is much larger than the width of their magnetic resonance. Examples of finite-field OPMs include both scalar and vector mode magnetometers in driven, relaxation, and free-induction decay modalities.

Zero-field OPMs operate in an effective magnetic field whose strength is smaller, or comparable, to the linewidth of the magnetic resonance of the atoms. It will be understood that a zero-field OPM need not operate in strictly zero magnetic field, but rather in a relatively low magnetic field as described in the preceding sentence. Examples of zero-field magnetometers include OPMs operating in SERF mode in either DC or modulated schemes. Zero-field magnetometers typically measure one or two vector components of the field and are among the most sensitive magnetometers to date. However, as their operation requires a low magnetic field environment, they are usually deployed inside expensive, bulky, and sophisticated magnetically shielded rooms.

In any OPM mode (SERF, vector, or scalar) magnetic noise should be considered. For instance, in one specific application of OPMs that involves measuring magnetic signals from the brain (i.e. magnetoencephalography or MEG), magnetic noise arises from oscillations of the magnetic field which have the same frequencies as neural signals and can overwhelm the magnetic signals of the brain. If these signals originate far from the region of interest (e.g., the human brain) then they can be suppressed by sampling and then subtracting the background field measured by a combination of two sensors. This technique is called gradiometry. First order gradiometer uses two sensors, second order three sensors, and so on. The higher the order the better background is suppressed but results in a more complicated system with many sensors that just measure background signal and don't contribute to the measurement of brain signal.

Conventional SERF mode systems have often used vapor cell magnetometers in combination with fluxgate or magnetoresistive magnetometers as a way to reach the SERF regime. Such implementations may use readings from the auxiliary sensor (for example, a fluxgate or magnetoresistive device) as error signals that are passed to magnetic coils, on a continuous or periodic or aperiodic basis, to modify or null the ambient background magnetic field at the position of the SERF mode magnetometer. Objectives of this active-shielding technique can include any of the following: i) suppression of the static and slowly varying components of the ambient background magnetic field so that the SERF mode magnetometer can operate within its dynamic range; ii) mitigation of spurious fast-varying fields that, while not bringing the SERF mode magnetometer outside its dynamic range, can be confounded with the target signal; and iii) active suppression of 60 Hz or 50 Hz power line noise that radiates from all alternating current power lines. The difference between 60 Hz and 50 Hz depends on the region of the world where this device is used. North America is 60 Hz while Europe and parts of Asia use 50 Hz. There can be challenges that may limit the performance and versatility of these SERF mode systems, such as, for example, poor common-mode background field rejection ratio due to the use of devices placed far apart from each other (for example, a few centimeters apart) such as in the use of a bulky SERF mode magnetometer and a bulky auxiliary sensor; and the limitation of the SERF mode magnetometer by intrinsic performance of the auxiliary sensor including, for example, (a) intrinsic noise of the auxiliary sensor (which can range, for example, from 1 pT/sqrt(Hz) for fluxgates to hundreds of pT/sqrt(Hz) for magnetoresistance devices, and is at least 1 to 3 orders of magnitude higher than what is required for MEG detection) which is translated to magnetic noise by a feedback loop or (b) the intrinsic offset of the auxiliary sensor (which may be of the order of 10 nT for both fluxgates and magnetoresistance devices and can be outside of the dynamic range of SERF mode magnetometers) which is translated to magnetic offset by a feedback loop.

In contrast to these conventional systems, systems and methods are described herein that combine SERF mode operation of an optically pumped magnetometer (OPM) with scalar or non-SERF vector mode magnetic field sensing using the same or a different OPM. This system and methods, in at least some embodiments, can enable, for example, wearable magnetoencephalography (MEG) sensing systems.

The term "non-SERF vector mode", as utilized to describe methods, systems, and other embodiments of the invention, will refer to a magnetometer operating in any vector mode other than the SERF mode.

A magnetic field measurement system, as described herein, can include one or more (for example, an array of) optically pumped magnetometers. In at least some embodiments, as described herein, the system can be arranged so that at least one (or even all) of the magnetometers can be operated sequentially in i) the scalar or non-SERF vector mode and ii) the SERF mode. In at least some embodiments, the system can be arranged so that at least one of the magnetometers can be operated in the scalar or non-SERF vector mode and at least one of the magnetometers can be operated in the SERF mode. In at least some of these embodiments, a scalar or non-SERF vector mode magnetometer and a SERF mode magnetometer may utilize the same vapor cell, as described below.

The magnetic field measurement systems described herein can be used to measure or observe electromagnetic signals generated by one or more sources (for example, biological sources). The system can measure biologically generated magnetic fields and, at least in some embodiments, can measure biologically generated magnetic fields in an unshielded or partially shielded environment. Aspects of a magnetic field measurement system will be exemplified below using magnetic signals from the brain of a user; however, biological signals from other areas of the body, as well as non-biological signals, can be measured using the system. Uses for this technology outside biomedical sensing include, but are not limited to, navigation, mineral exploration, non-destructive testing, detection of underground devices, asteroid mining, and space applications. In at least some embodiments, the system can be a wearable MEG system that can be used outside a magnetically shielded room.

FIG. 1A is a block diagram of components of one embodiment of a magnetic field measurement system 140. The system 140 can include a computing device 150 or any other similar device that includes a processor 152 and a memory 154, a display 156, an input device 158, one or more magnetometers 160, one or more magnetic field generators 162, and, optionally, one or more sensors 164. The system 140 and its use and operation will be described herein with respect to the measurement of neural signals arising from signal sources in the brain of a user as an example. It will be understood, however, that the system can be adapted and used to measure other neural signals, other biological signals, as well as non-biological signals.

The computing device 150 can be a computer, tablet, mobile device, field programmable gate array (FPGA), microcontroller, or any other suitable device for processing information. The computing device 150 can be local to the user or can include components that are non-local to the user including one or both of the processor 152 or memory 154 (or portions thereof). For example, in at least some embodiments, the user may operate a terminal that is connected to a non-local computing device. In other embodiments, the memory 154 can be non-local to the user.

The computing device 150 can utilize any suitable processor 152 including one or more hardware processors that may be local to the user or non-local to the user or other components of the computing device. The processor 152 is configured to execute instructions, as described below.

Any suitable memory 154 can be used for the computing device 150. The memory 154 illustrates a type of computer-readable media, namely computer-readable storage media. Computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 156 can be any suitable display device, such as a monitor, screen, or the like, and can include a printer. In some embodiments, the display is optional. In some embodiments, the display 156 may be integrated into a single unit with the computing device 150, such as a tablet, smart phone, or smart watch. In at least some embodiments, the display is not local to the user. The input device 158 can be, for example, a keyboard, mouse, touch screen, track ball, joystick, voice recognition system, or any combination thereof, or the like. In at least some embodiments, the input device is not local to the user.

The magnetic field generator(s) 162 can be, for example, Helmholtz coils, solenoid coils, planar coils, saddle coils, electromagnets, permanent magnets, or any other suitable arrangement for generating a magnetic field. The optional sensor(s) 164 can include, but are not limited to, one or more magnetic field sensors, position sensors, orientation sensors, accelerometers, image recorders, or the like or any combination thereof.

The one or more magnetometers 160 can be any suitable magnetometer including, but not limited to, any suitable optically pumped magnetometer. In at least some embodiments, at least one of the one or more magnetometers (or all of the magnetometers) of the system is arranged for operation in both i) the scalar or non-SERF vector mode and ii) the SERF mode. Alternatively or additionally, the one or more magnetometers 160 of the system include at least one scalar or non-SERF vector mode magnetometer and at least one SERF mode magnetometer. Examples of dual mode systems are disclosed in U.S. Patent Provisional Patent Application Ser. No. 62/723,933, incorporated herein by reference in its entirety.

As a further example of an optically pumped magnetometer that can operate in both i) the scalar or non-SERF vector mode and ii) the SERF mode, an alkali metal magnetometer can be operated as a zero-field magnetometer with the ability to operate in SERF mode with suppressed spin-exchange relaxation. At finite magnetic fields, such that the Larmor precession frequency is much higher than the intrinsic spin relaxation, the same magnetometer can be used to measure the magnitude of the magnetic field when the magnetometer is operating in the scalar mode (or the non-SERF vector mode).

Figure 1B:
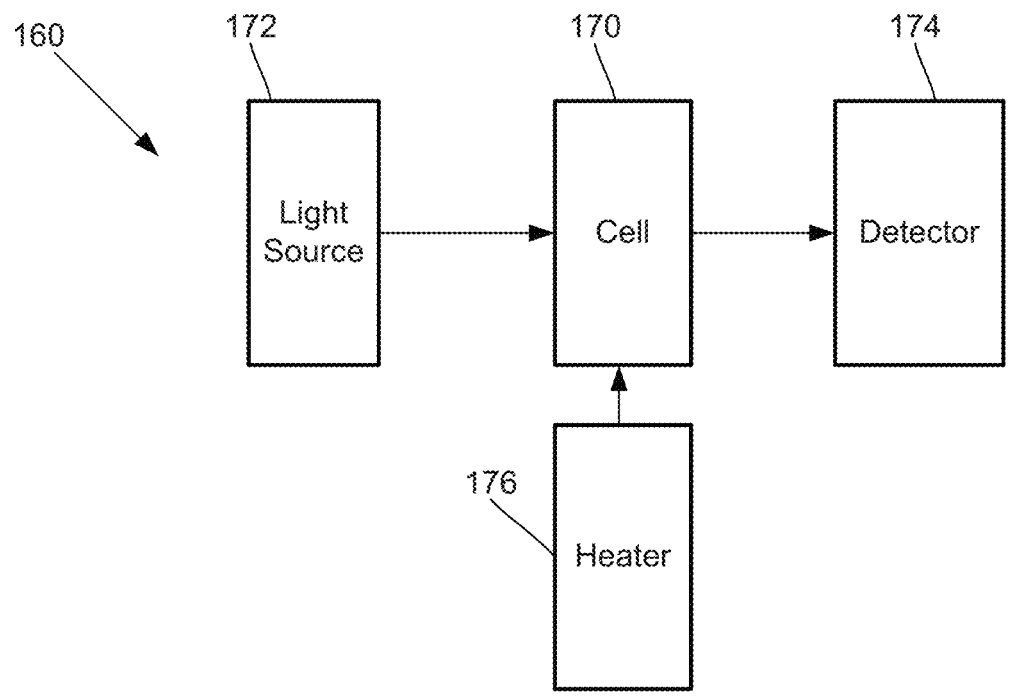
FIG. 1B is a schematic block diagram of one embodiment of a magnetometer, according to the invention.

FIG. 1B is a schematic block diagram of one embodiment of a magnetometer 160 which includes an alkali metal gas cell 170 (also referred to as a "cell"); a heating device 176 to heat the cell 170; a light source 172; and a detector 174. The gas cell 170 can include, for example, an alkali metal vapor (for example, rubidium in natural abundance, isotopically enriched rubidium, potassium, or cesium, or any other suitable alkali metal such as lithium, sodium, or francium), quenching gas (for example, nitrogen) and buffer gas (for example, nitrogen, helium, neon, or argon). The light source 172 can include, for example, a laser to optically pump the alkali metal atoms and to probe the gas cell, as well as optics (such as lenses, waveplates, collimators, polarizers, and objects with reflective surfaces) for beam shaping and polarization control and for directing the light from the light source to the cell and detector. The detector 174 can include, for example, an optical detector to measure the optical properties of the transmitted light field amplitude, phase, or polarization, as quantified through optical absorption and dispersion curves, spectrum, or polarization or the like or any combination thereof.

In a scalar mode magnetometer (e.g., an optically pumped magnetometer operating in the scalar mode), in addition to the above elements, a local oscillator (LO) (see, for example, FIG. 9) is added to drive the spin precession on resonance with the Larmor frequency as set by the given ambient field. The excitation can be introduced in the form of an RF field generated using the magnetic field generator 162 or optically by modulating the intensity, frequency, or polarization of the pumping light beam from the light source 172.

Examples of suitable light sources include, but are not limited to, a diode laser (such as a vertical-cavity surface-emitting laser (VCSEL), distributed Bragg reflector laser (DBR), or distributed feedback laser (DFB)), light-emitting diode (LED), lamp, or any other suitable light source. Examples of suitable detectors include, but are not limited to, a photodiode, charge coupled device (CCD) array, CMOS array, camera, photodiode array, single photon avalanche diode (SPAD) array, avalanche photodiode (APD) array, or any other suitable optical sensor array that can measure the change in transmitted light at the optical wavelengths of interest.

Examples of magnetic field measurement systems or methods of making such systems or components for such systems are described in U.S. Provisional Patent Application Ser. Nos. 62/689,696; 62/699,596; 62/719,471; 62/719,475; 62/719,928; 62/723,933; 62/732,327; 62/732,791; 62/741,777; 62/743,343; 62/745,144; 62/747,924; and 62/752,067, all of which are incorporated herein by reference in their entireties.

Figure 1C:
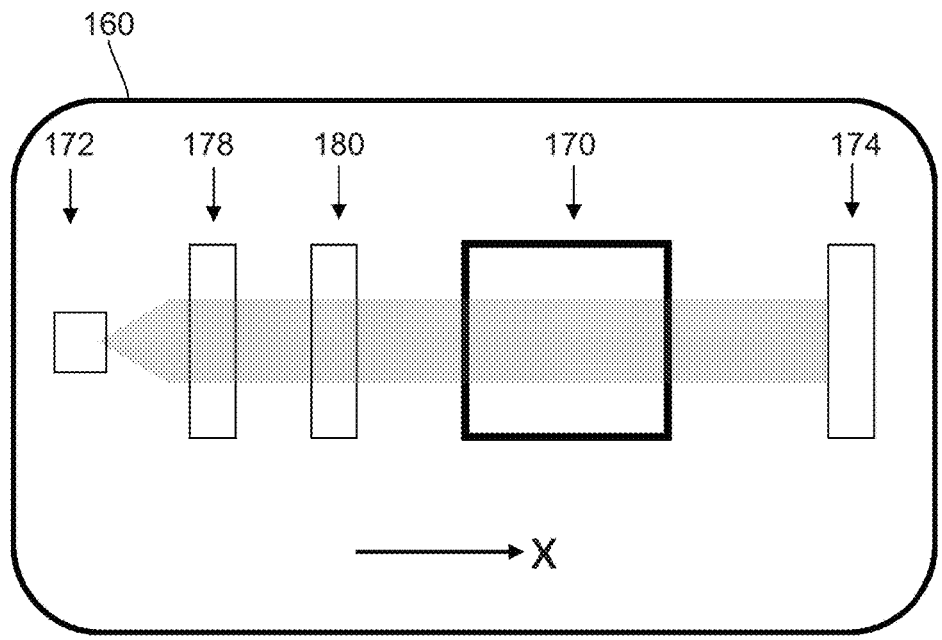
FIG. 1C is a schematic block diagram of one embodiment of optical element of a magnetometer, according to the invention.

FIG. 1C illustrates one example of am optically pumped magnetometer (OPM) 160 that includes a light source 172, a converging lens 178, a wave retarder 180, a vapor cell 170, and a detector 174. The light source 172 (for example, a distributed feedback laser (DFB), vertical cavity surface-emitting laser (VCSEL), or edge emitting laser diode) radiates light at its intrinsic beam divergence angle. The converging lens 178 can be used to collimate the light into a parallel path. The light is transformed from linearly to circularly polarized via the wave retarder 180 (for example, a quarter wave plate). The light passes through the alkali metal vapor in the gas cell 170 and is rotated or absorbed by the alkali metal vapor before being received by the detector 174.

Figure 2:
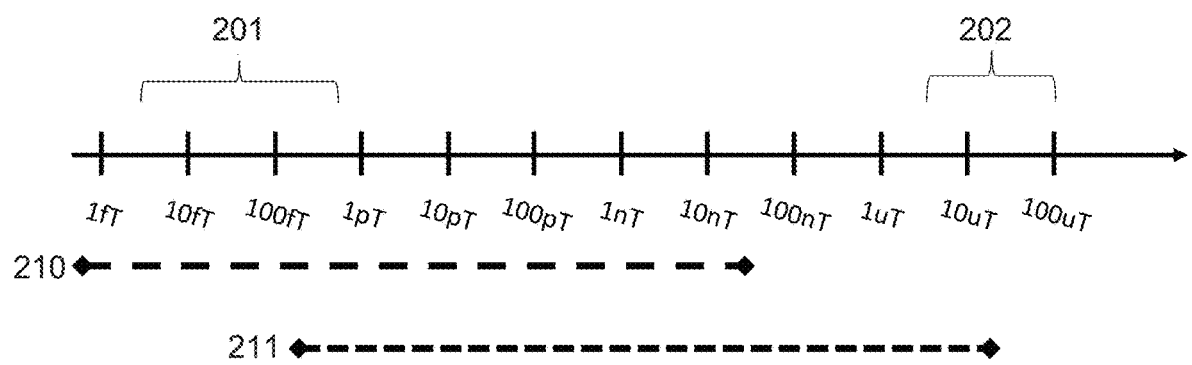
FIG. 2 shows a magnetic spectrum with lines indicating dynamic ranges of magnetometers operating in different modes.

FIG. 2 shows the magnetic spectrum from 1 fT to 100 μT in magnetic field strength on a logarithmic scale. The magnitude of magnetic fields generated by the human brain are indicated by range 201 and the magnitude of the background ambient magnetic field, including the Earth's magnetic field, by range 202. The strength of the Earth's magnetic field covers a range as it depends on the position on the Earth as well as the materials of the surrounding environment where the magnetic field is measured. Range 210 indicates the approximate measurement range of a magnetometer operating in the SERF mode (e.g., a SERF magnetometer) and range 211 indicates the approximate measurement range of a magnetometer operating in the scalar mode (e.g., a scalar magnetometer.) Typically, a SERF magnetometer is more sensitive than a scalar magnetometer but many conventional SERF magnetometers typically only operate up to about 20 to 200 nT while the scalar magnetometer starts in the 100 fT range but extends above 10 μT. At very high magnetic fields the scalar magnetometer typically becomes nonlinear due to a nonlinear Zeeman splitting of atomic energy levels.

Figure 3A:
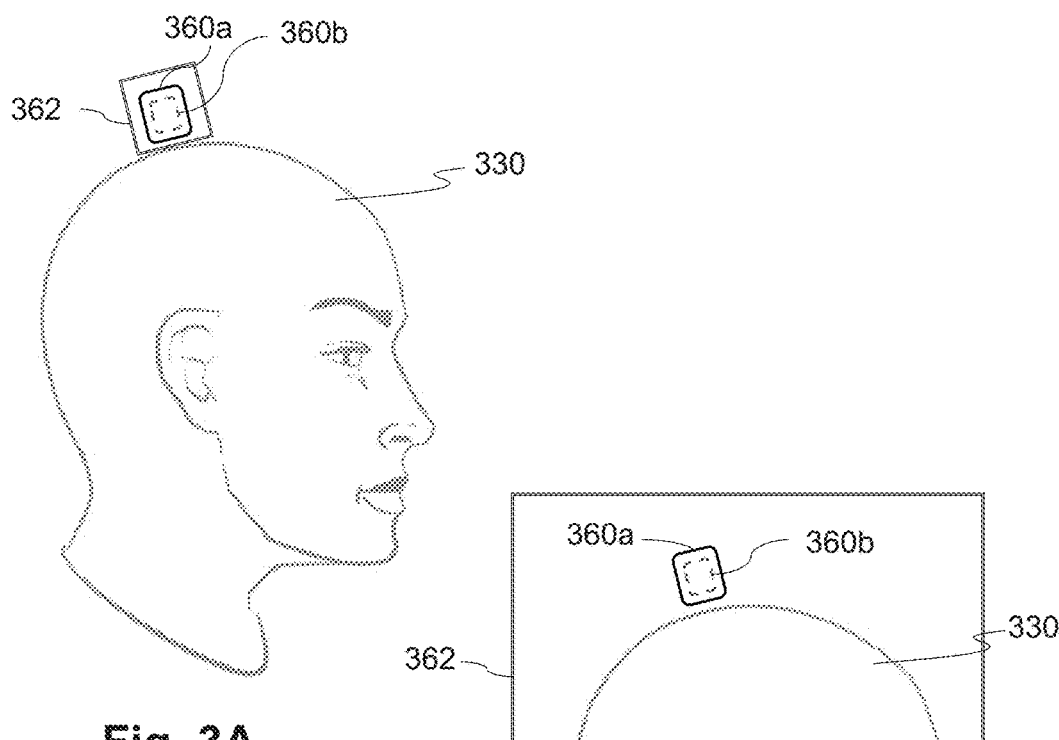
FIG. 3A is a schematic view of one embodiment of a dual arrangement of a SERF mode magnetometer and a scalar mode magnetometer, according to the invention.

FIG. 3A illustrates a dual arrangement with a SERF mode magnetometer 360a and a scalar or non-SERF vector mode magnetometer 360b in combination with a magnetic field generator 362. As an example, this dual arrangement could be placed on the scalp 330 of a user to measure MEG. In at least some embodiments, the magnetometers 360a, 360b are at the same location as the two magnetometers both use the same alkali vapor cell or the two magnetometers are actually the same magnetometer operating sequentially in i) the scalar or non-SERF vector mode and ii) the SERF mode. In other embodiments, the magnetometers 360a, 360b are separate from each other, but are preferably located close together.

Figure 3B:
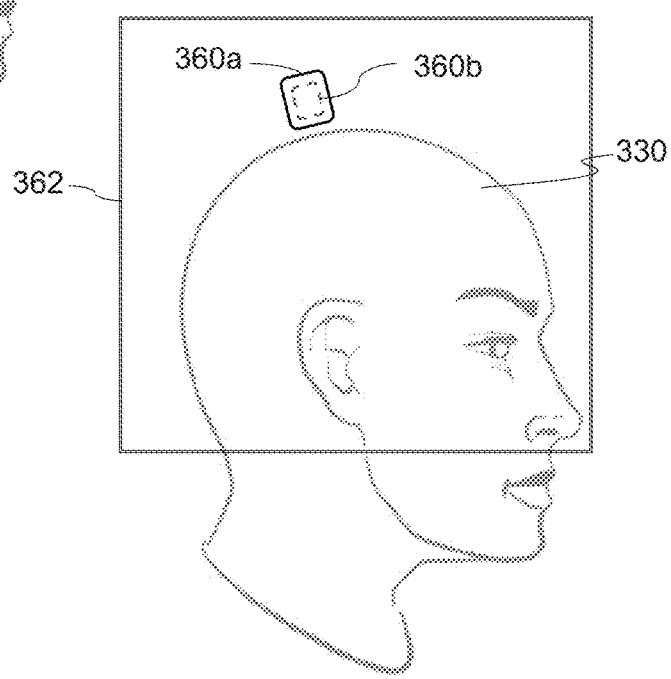
FIG. 3B is a schematic view of another embodiment of a dual arrangement of a SERF mode magnetometer and a scalar mode magnetometer, according to the invention.

FIG. 3B illustrates a dual arrangement of SERF mode magnetometer 360a and a scalar or non-SERF vector mode magnetometer 360b in combination with a magnetic field generator 362 that is placed around a portion of the user's head 330.

Figure 3C:
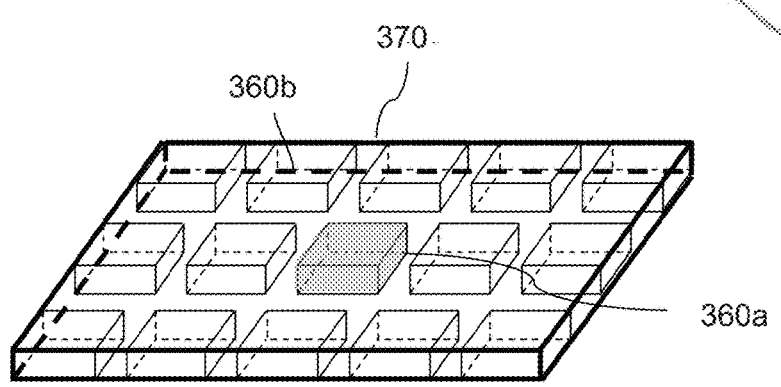
FIG. 3C is a schematic view of a vapor cell of yet another embodiment of a dual arrangement of a SERF mode magnetometer and a scalar mode magnetometer, according to the invention

As described in more detail below, the dual arrangement of a SERF mode magnetometer 360a and a scalar or non-SERF vector mode magnetometer 360b can include, but is not limited to, a) a single magnetometer that alternates operation in i) the SERF mode and ii) the scalar or non-SERF vector mode or b) an arrangement using a single vapor cell with a first portion of the vapor cell operating as a SERF mode magnetometer and a second portion of the vapor cell operation as a scalar or non-SERF vector mode magnetometer. Examples of the later arrangement can be found in U.S. Provisional Patent Application Ser. Nos. 62/699,596 and 62/732,327, both of which are incorporated herein by reference in their entireties. FIG. 3C also illustrates a vapor cell 370 where a portion of the vapor cell forms a SERF mode magnetometer 360a because the ambient background magnetic field at that portion has been reduced sufficiently that the portion can operate in the SERF mode. Other portions of the vapor cell 370 can operate as a scalar or non-SERF vector mode magnetometer 360b. In other embodiments, the magnetometers 360a, 360b are separate from each other, but are preferably located close together.

The systems and methods as described herein utilize active shielding by employing the magnetic field generators 362. It will be understood, however, that the systems and methods may also include passive shielding using materials such as mu-metal and ferrite or any other suitable components. Examples of passive shielding are found in U.S. Provisional Patent Application Ser. Nos. 62/719,928 and 62/752,067, all of which are incorporated herein by reference in their entireties.

Figure 4:
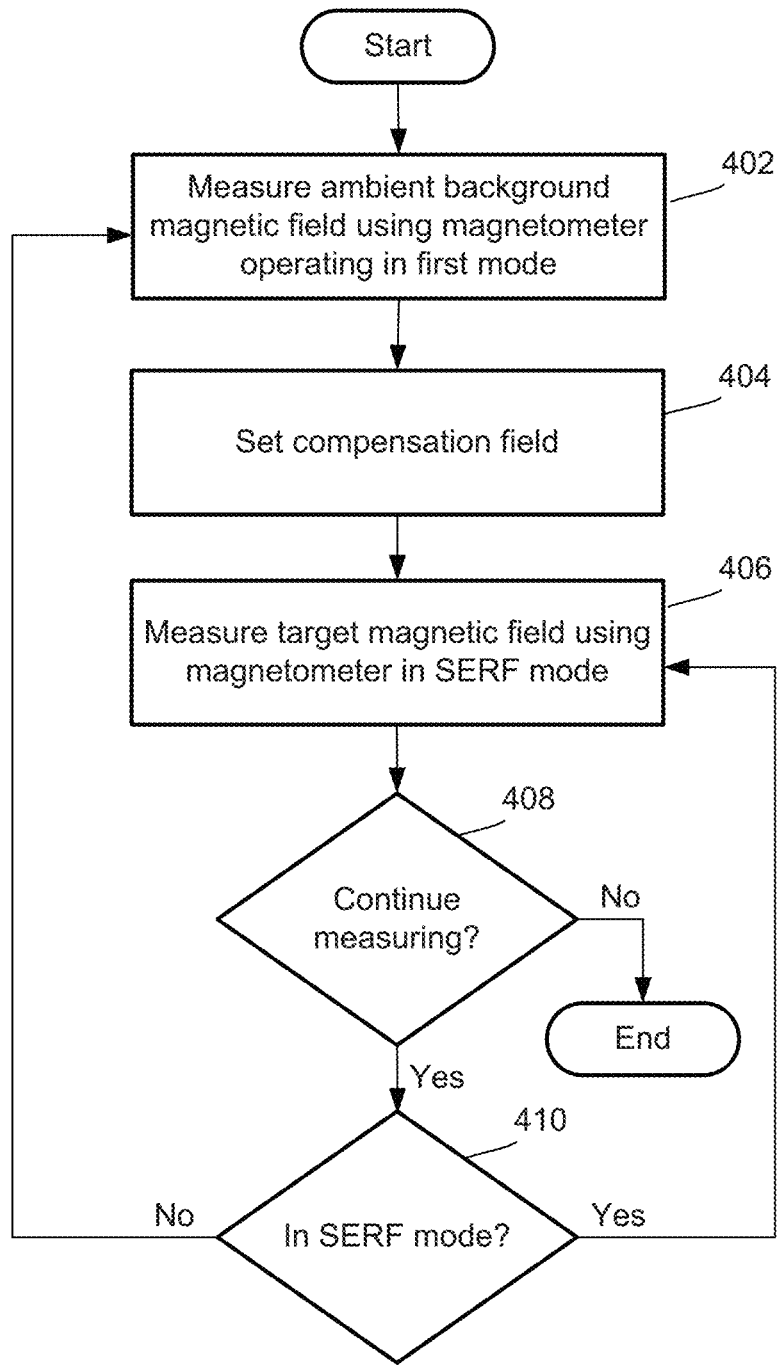
FIG. 4 is a flowchart of one embodiment of method of operating a magnetic field measurement system, according to the invention.

FIG. 4 illustrates one embodiment of a method of operation or use of a magnetic field measurement system that contains a dual arrangement of a SERF mode magnetometer and a scalar or non-SERF vector mode magnetometer, as well as active shielding using a magnetic field generator or the like, as illustrated in FIGS. 3A and 3B. In step 402, the ambient background magnetic field is measured using the magnetometer operating in a first mode selected from a scalar mode or a non-SERF vector mode. In step 404, this ambient background field is canceled, or reduced substantially (e.g., by at least 80, 90, 95, or 99 percent) by the application of a compensation field (i.e., a local field) using the magnetic field generator. The compensation field may be, for example, equal and opposite to the ambient background magnetic field or at least 80, 90, 95, or 99 percent of the ambient background magnetic field.

In step 406, the system can measure the vector components of the magnetic field due to neural activity (or any other target magnetic field of interest) using a magnetometer operating in a SERF mode different from the first mode. In step 408, the system or user determines whether to continue measuring. If no, then the system ends operation. If yes, then in step 410 the system determines whether the magnetometer continues to operate in SERF mode. If yes, the system returns to step 406 to make another measurement. If no, such as when the compensation field is no longer sufficient to reduce the ambient background magnetic field to a magnitude that allows the magnetometer to operate in SERF mode (for example, 200 nT, 50 nT, 20 nT, or less), then the system returns to step 402 to measure the ambient background magnetic field and, in step 404, modify or otherwise alter the compensation field.

As an example of step 410, in at least some embodiments, the system is configured to determine when SERF mode is lost (for example, by comparing transmitted light level as measured by the detector with respect to a threshold value or flatness of response. The SERF mode may be lost when, for example, the ambient background magnetic field undergoes a rapid change in amplitude or direction (or both).

As an alternative to step 410, the system may automatically switch from the SERF mode to the scalar or non-SERF vector mode periodically (for example, at a specific or selected repetition rate) or aperiodically to perform steps 402 and 404 again. In some embodiments, this switching between modes may occur at least every 0.5, 1, 2, 5, 10, 50, 100, or 500 milliseconds or every 0.5, 1, 2, 5, 10, or 30 seconds or every 1, 2, 5, or 10 minutes.

Figure 5:
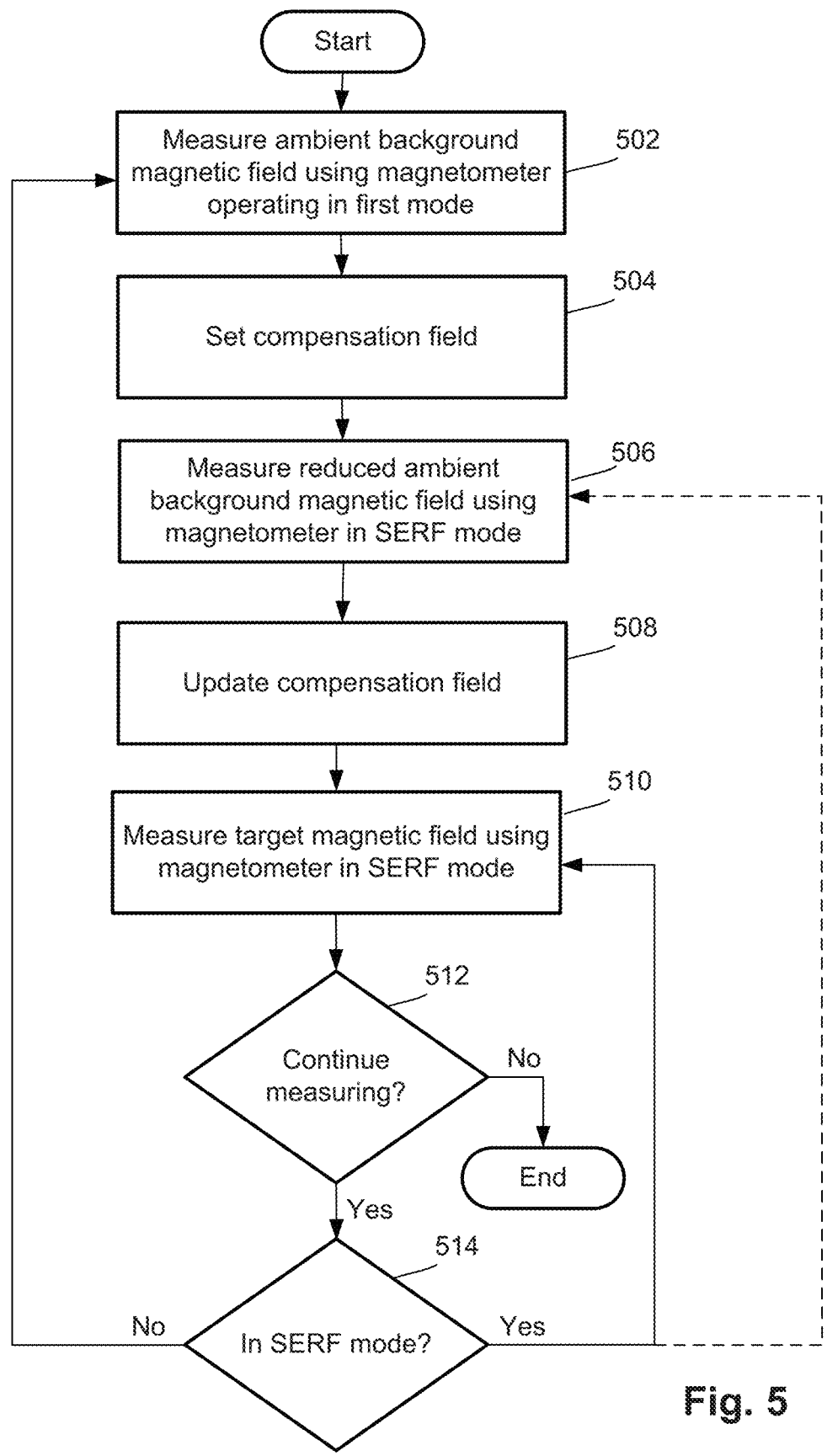
FIG. 5 is a flowchart of another embodiment of method of operating a magnetic field measurement system, according to the invention.

FIG. 5 illustrates another embodiment of a method of operation or use of a magnetic field measurement system that contains a dual arrangement of a SERF mode magnetometer and a scalar or non-SERF vector mode magnetometer, as well as active shielding using a magnetic field generator or the like, as illustrated in FIGS. 3A and 3B. In step 502, the ambient background magnetic field is measured using the magnetometer operating in a first mode selected from a scalar mode or a non-SERF vector mode. In step 504, this ambient background field is canceled, or reduced substantially (e.g., by at least 80, 90, 95, or 99 percent) by the application of a compensation field (i.e., a local field) using the magnetic field generator. The compensation field may be, for example, equal and opposite to the ambient background magnetic field or at least 80, 90, 95, or 99 percent of the ambient background magnetic field.

In step 506, a second measurement of the ambient background magnetic field (as reduced by the compensation field—i.e., the reduced ambient background magnetic field) is performed using a magnetometer operating in a SERF mode different from the first mode. In step 508, in response to this second measurement, the compensation field can be altered or updated to 'fine-tune' the cancellation or reduction of the ambient background magnetic field.

In step 510, the system can measure the vector components of the magnetic field due to neural activity (or any other target magnetic field of interest) using the magnetometer operating in the SERF mode. In step 512, the system or user determines whether to continue measuring. If no, then the system ends operation. If yes, then in step 514 the system determines whether the magnetometer continues to operate in SERF mode. If yes, the system returns to step 510 to make another measurement or, optionally (indicated by the dotted line in FIG. 5), the system returns to step 506 to again measure the reduced ambient background magnetic field with the magnetometer in SERF mode to update the compensation field. If the magnetometer is no longer operating in SERF mode in step 514, such as when the compensation field is no longer sufficient to reduce the ambient background magnetic field to a magnitude that allows the magnetometer to operate in SERF mode (for example, 200 nT, 50 nT, 20 nT, or less), then the system returns to step 502 to measure the ambient background magnetic field and, in step 504, modify or otherwise alter the compensation field.

One embodiment of a magnetic field measurement system that includes an optically pumped magnetometer 160 (FIG. 1A) that can operate in both i) SERF mode and ii) scalar or non-SERF vector mode at interleaved periods of time using the same vapor cell 170 (FIG. 1B). This approach has the advantage of in situ-magnetometry and compensation or, in other words, the ambient background magnetic field is measured at the same location as the magnetometer that measures the biological or other signal of interest. Alternatively, the magnetic field measurement system includes a vapor cell that can be used for both a SERF mode magnetometer and a scalar or non-SERF vector mode magnetometer as illustrated in FIG. 3C. In other embodiments, the magnetometers are separate from each other, but are preferably located close together.

In at least some embodiments, these magnetic field measurement systems can operate according to either of the methods illustrated in FIG. 4 or 5, as described above. For example, when the user initially starts up the system (for example, a wearable MEG system) the ambient background magnetic field is measured using a magnetometer in scalar or non-SERF vector mode. Next, the system applies a compensation field using the magnetic field generator (for example, active shielding electromagnets such as Helmholtz coils.) Then the system switches to SERF mode and optionally performs a measurement of the reduced ambient background magnetic field. In at least some embodiments, this high-accuracy measurement allows the system to update the cancellation field to compensate for small changes in the ambient background magnetic field.

With the system operating in SERF mode, the magnetometer then measures neural activity or other biosignal or signal of interest. In at least some embodiments, the system continues to measure the signal of interest until the compensation field no longer sufficiently reduces the ambient background magnetic field so that the SERF mode is disrupted. Then the system switches back to using scalar or non-SERF vector magnetometry to again measure the ambient background magnetic field and adjust or modify the compensation field so that SERF mode operation is again possible. In at least some embodiments, if the background field drifts slowly the shift will be measured in SERF mode and the compensation coils updated accordingly without leaving SERF mode.

Figure 6:
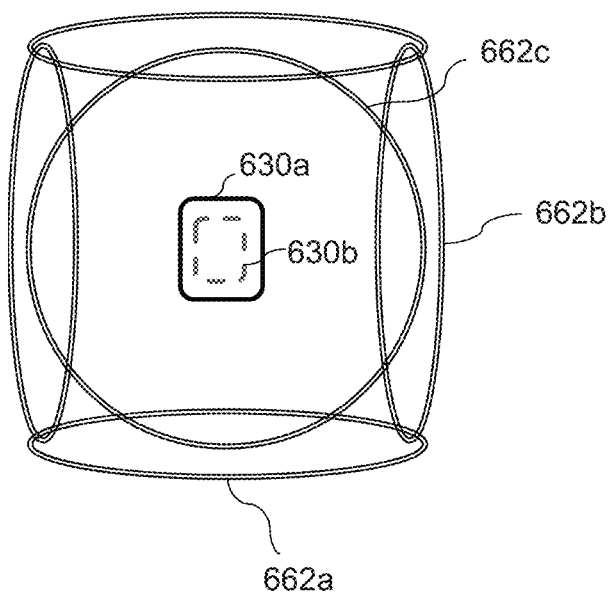
FIG. 6 is a schematic view of yet another embodiment of a dual arrangement of a SERF mode magnetometer and a scalar mode magnetometer along with graphs showing a resulting measured magnetic field with sweeping of applied magnetic fields along the respective axes, according to the invention.
Figure 6:
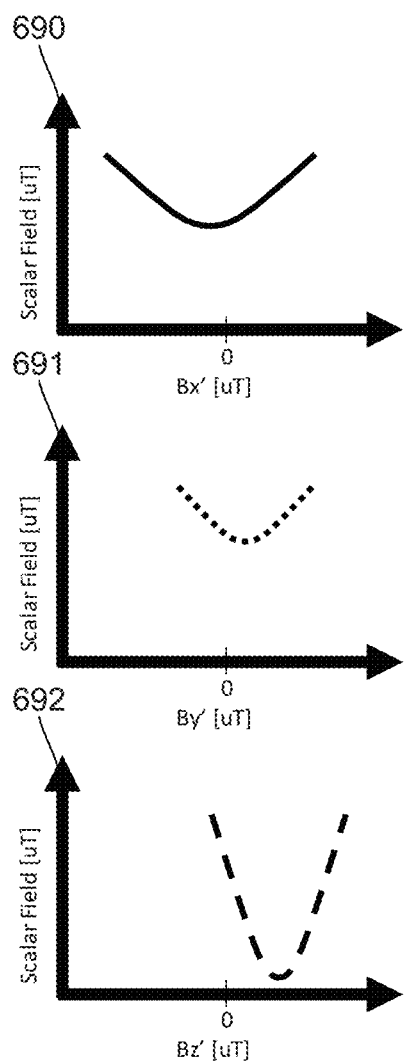

Referring now to FIG. 6, the system (or any other system described herein) can utilize a dual OPM arrangement 660a, 660b (an arrangement of one or more magnetometers which can operate in i) SERF mode and ii) scalar or non-SERF vector mode, as described above) surrounded by three pairs of compensation coils 662a, 662b, 662c which can generate the three components, Bx', By', Bz', respectively, of the compensation magnetic field to cancel or reduce the ambient background magnetic field (including the Earth's magnetic field). When in the scalar mode, the OPM only measures the magnitude of the ambient background magnetic field but it cannot directly determine the individual three vector components. In other words, the scalar magnetometer measures $(Bx^2+By^2+Bz^2)^{1/2}$ where Bx, By and Bz are the three Cartesian components of the ambient background magnetic field. To individually measure the three vector components, the magnetic field produced by the three pairs of compensation coils 662a, 662b, 662c can be individually swept to find the minimum of the resulting field, as illustrated in graphs 690, 691, 692, which corresponds to sweeping through the three vector components, Bx', By', Bz', respectively. Each of the graphs 690, 691, 692 illustrate the measured field magnitude versus the swept vector component with the minimum corresponding to the swept vector component approximately equaling the corresponding vector component of the ambient background magnetic field.

In another embodiment, the scalar mode magnetometer measures the magnitude of the ambient background magnetic field, $|B|=(Bx^2+By^2+Bz^2)^{1/2}$ where Bx, By and Bz are the three Cartesian components of the ambient background magnetic field. The magnetic field vector generated by the system using the magnetic field generator is given by: $B'=xBx'+yBy'+zBz'$ where x, y and z are Cartesian unit vectors. In a configuration where the laser is oriented along the x-axis of the system, to measure the By component of the background field, the y-axis magnetic field, By', is swept over a range of values, for example, −10 μT to 10 μT and |B| is measured. $|B|=(Bx+(By^2+By'^2)+Bz^2)^{1/2}$. The output of the detector is a Lorentzian function with a peak at By'=−By. $By^C$ is set at this value. This procedure can be repeated to find Bz. Bx is found by first zeroing By and Bz by applying $By^C$ and $Bz^C$ then sweeping Bx' over the range of interest. When By'=−By the output of the detector reaches a minimum in an inverted Lorentzian. $Bx^C$ is set to the value of Bx' when the minimum occurs. In some instances, an additional oscillating component added to Bx' may be employed to increase the sensitivity of accuracy of the $By^C$ and $Bz^C$ measurements by narrowing the Lorentzian response.

In other embodiments, the system includes an optically pumped magnetometer that can be operated in SERF mode, an optically pumped magnetometer (the same or different from the first magnetometer) that can be operated in the scalar or non-SERF vector mode, and one or more auxiliary sensors, such as a fluxgate or magnetoresistance device. In at least some embodiments, the one or more auxiliary sensors can be operated concurrently, or at interleaved periods of time with the magnetometer(s). In at least some embodiments, the one or more auxiliary sensors can be operated continually or periodically. In at least some embodiments, the one or more auxiliary sensors can be used to measure the ambient background magnetic field with these measurements can be used to produce the compensation field and the magnetometer operating in the scalar or non-SERF vector mode can be used from time to time to recalibrate the one or more auxiliary sensors. This calibration is useful because the one or more auxiliary sensors are located at a distance from the magnetometer operating in the SERF mode, whereas the magnetometer operating in the scalar or non-SERF vector mode can be the same magnetometer or use the same vapor cell or located near the magnetometer operating in SERF mode. In at least some embodiments, an advantage of the approach is that measurements with the auxiliary sensors may be faster, thus reducing the time between consecutive SERF measurements and measurement bandwidths.

Figure 7A:
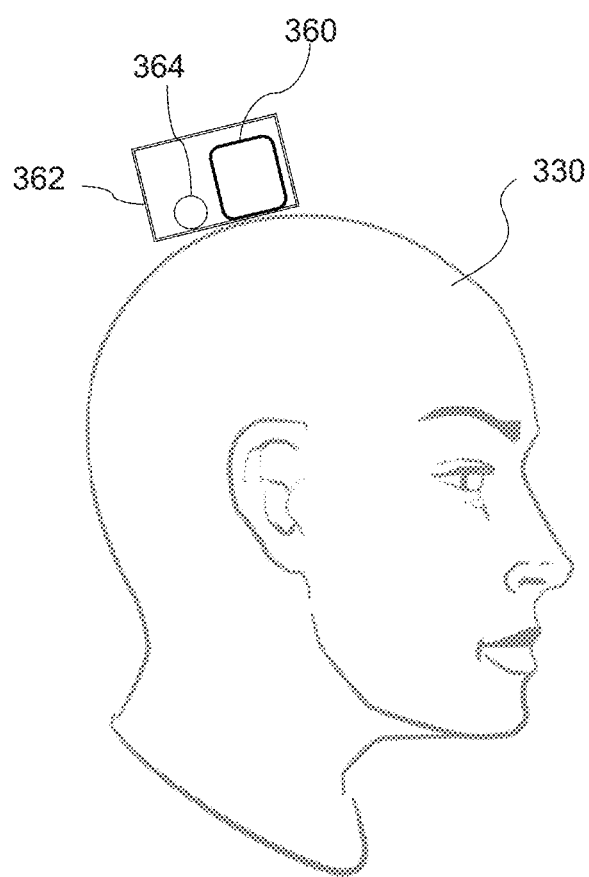
FIG. 7A is a schematic view of one embodiment of an arrangement of a magnetometer and an auxiliary sensor, according to the invention.
Figure 7B:
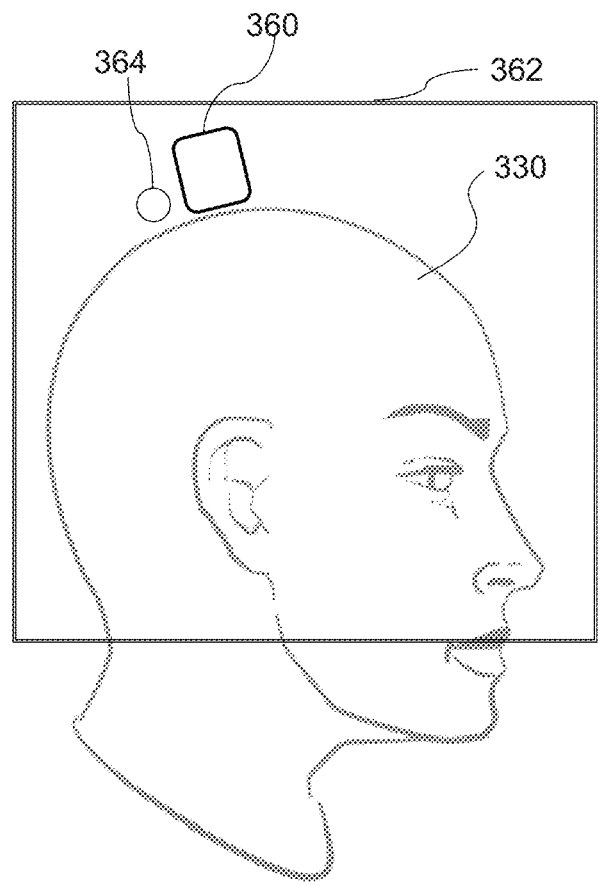
FIG. 7B is a schematic view of another embodiment of an arrangement of a magnetometer and an auxiliary sensor, according to the invention.

FIGS. 7A and 7B illustrate two embodiments of arrangements that are similar to those illustrated in FIGS. 3A and 3B, respectively, except that these arrangements include an auxiliary sensor 364 such as a magnetoresistance device or fluxgate sensor, in addition to the magnetometer(s) 360 and magnetic field generator 162 of FIG. 1A.

Figure 8:
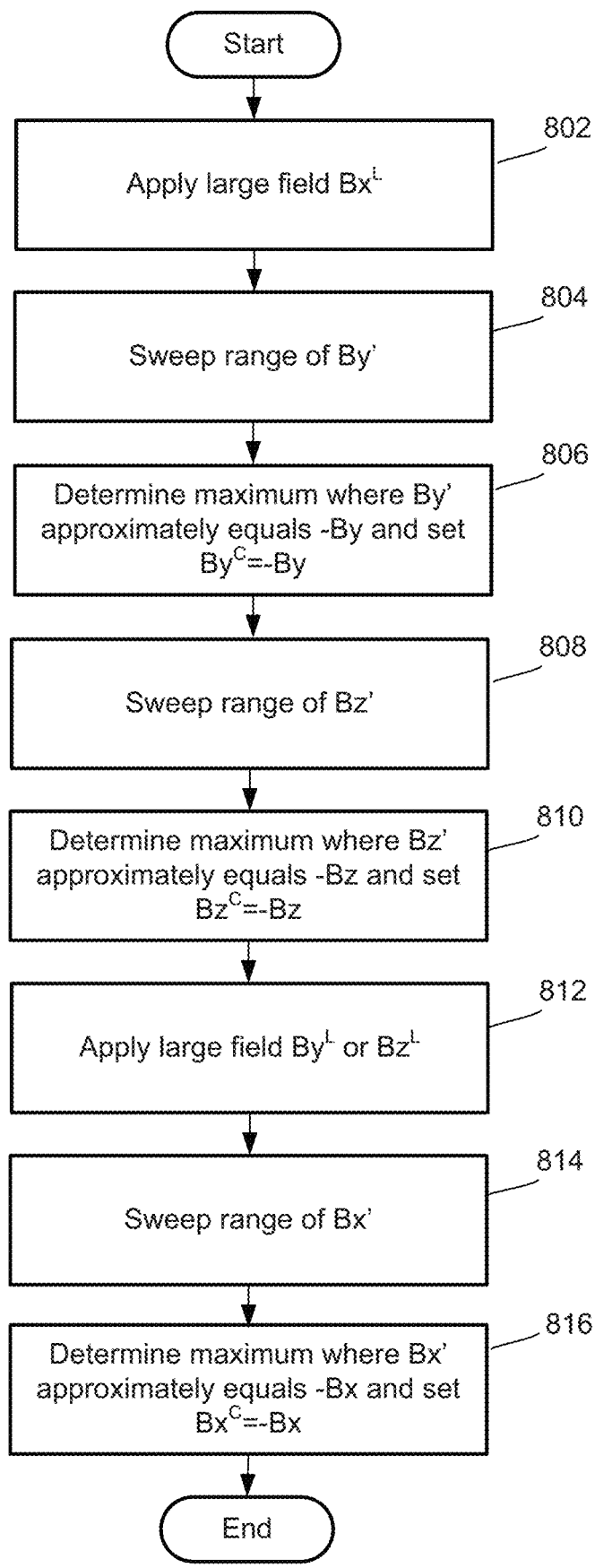
FIG. 8 is a flowchart of one embodiment of method of determining a compensation field, according to the invention.

There are a variety of methods and techniques for determining the ambient background magnetic field and setting a compensation field. FIG. 8 illustrates one embodiment of such a method which can, at least in some embodiments, be used for steps 402 and 404 in FIG. 4 or steps 502 and 504 in FIG. 5.

In at least some embodiments, this method uses intensity measurements from an optically pumped magnetometer operating with a single pump/probe laser as the light source and with a single photodiode as the detector (although other light sources and detectors can be used). When the total magnetic field is aligned with the pump axis (in this case, designated to be the x-axis) the measured optical signal intensity is maximum. Accordingly, if any component of the magnetic field appears along the y or z axes, the measured optical transmitted intensity (TI) will be reduced. It will be understood that the x, y, and z axes described below are interchangeable meaning that the x axis can be replaced by the y or z axes and so on.

The ambient background magnetic field can be determined by varying the applied fields By' and Bz' until the total intensity is maximum. When this occurs By'~−By and Bz'~−Bz Turning to FIG. 8, in step 802 a large field, $Bx^L$, is applied by the system where $Bx^L$ is larger than the background Bx to ensure $Bx+Bx^L$ is not zero. For example, if Bx could be any value from −5 μT to 5 μT then adding a $Bx^L$ of 10 uT would results in a non-zero range from 5 μT to 15 μT.

In step 804, By' is swept along the range of possible By. If the range of expected By were from −5 μT to 5 μT then By' might be swept from −6 μT to 6 μT. In step 806, the transmitted intensity (TI) is monitored during the sweep and the maximum is found when By'~−By. $By^C$ is then set to −By, the value that provided the maximum TI. When this is done the total field along the y-axis is zero; $By+By^C=0$.

In step 808 Bz' is swept over the expected range of Bz. In step 810, the transmitted intensity (TI) is monitored during the sweep and the maximum is found when Bz'~−Bz. Once the maximum TI value is found $Bz^C$ is set to −Bz. When this is done, $Bz+Bz^C=0$. If completed, there is no remaining magnetic field along the y or z axes.

In steps 812 to 816, Bx is determined. In step 812, a large background field, $By^L$, is applied along the y-axis (or equivalently on the z-axis), similar to step 802, and then in step 814 Bx' is swept over the expected range. In step 816, the transmitted intensity (TI) is monitored during the sweep and the maximum is found when Bx'~−Bx. Once the maximum TI value is found $Bx^C$ is set to −Bx. When this is done, The total magnetic field along the x-axis is zero: $Bx+Bx^C=0$.

Using this procedure in steps 802 to 816, the compensation fields $Bx^C$, $By^C$, $Bz^C$ are determined and can be applied using the magnetic field generators with the result that the total remaining magnetic fields from the combination of the background field the and correction fields along each Cartesian axis are all equal zero or are near zero (for example, a reduction of at least 80, 90, 95, or 99 percent in the ambient background magnetic field.)

Figure 9:
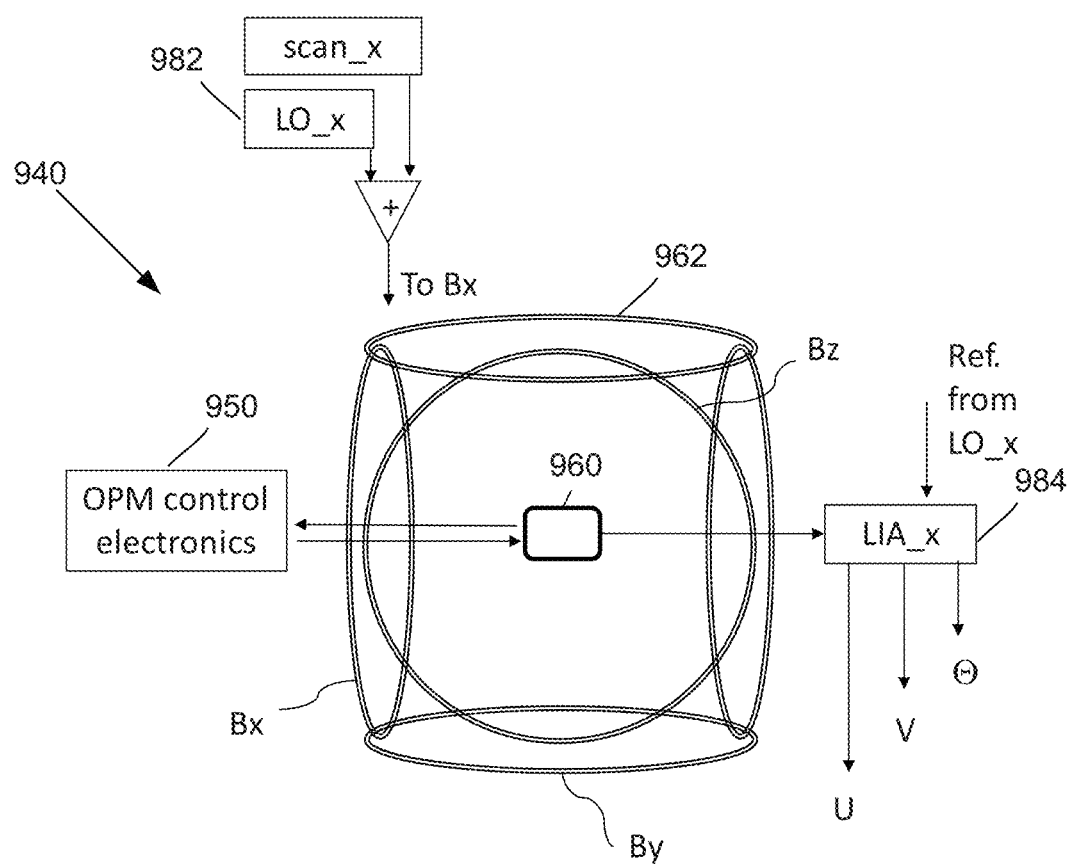
FIG. 9 is a schematic view of one embodiment of an arrangement of a magnetometer, magnetic field generators, a local oscillator, and a lock-in amplifier, according to the invention.

Other embodiments for determining a compensation field utilize a lock-in amplifier. FIG. 9 illustrates one embodiment of a portion of a magnetic field measurement system 940 with a computing device 950 (designated as the "OPM control electronics"), a magnetometer 960, and a magnetic field generator 962 disposed around the magnetometer. The magnetic field generator 962 includes three pairs of coils (labeled Bx, By, and Bz) and arranged to produce three fields Bx', By', and Bz'. The embodiment illustrated in FIG. 9 has a local oscillator (LO_x) 982 applied to the coils Bx so that the coils Bx can generate an RF field with a frequency ho can be swept as described below. The embodiment illustrated in FIG. 9 also includes a lock-in amplifier (LIA_x) 984 that receives input from the detector of the magnetometer 960 and the local oscillator 982 and can be used to provide in-phase ("U"), quadrature ("V"), and phase angle ("θ") outputs based on the inputs, as described in more detail below.

In at least some embodiments, the systems or methods may utilize techniques, such as, but not limited to, least square fitting, filtering, and machine learning, to infer magnetic fields based on sensor outputs and field-generator inputs.

Figure 10:
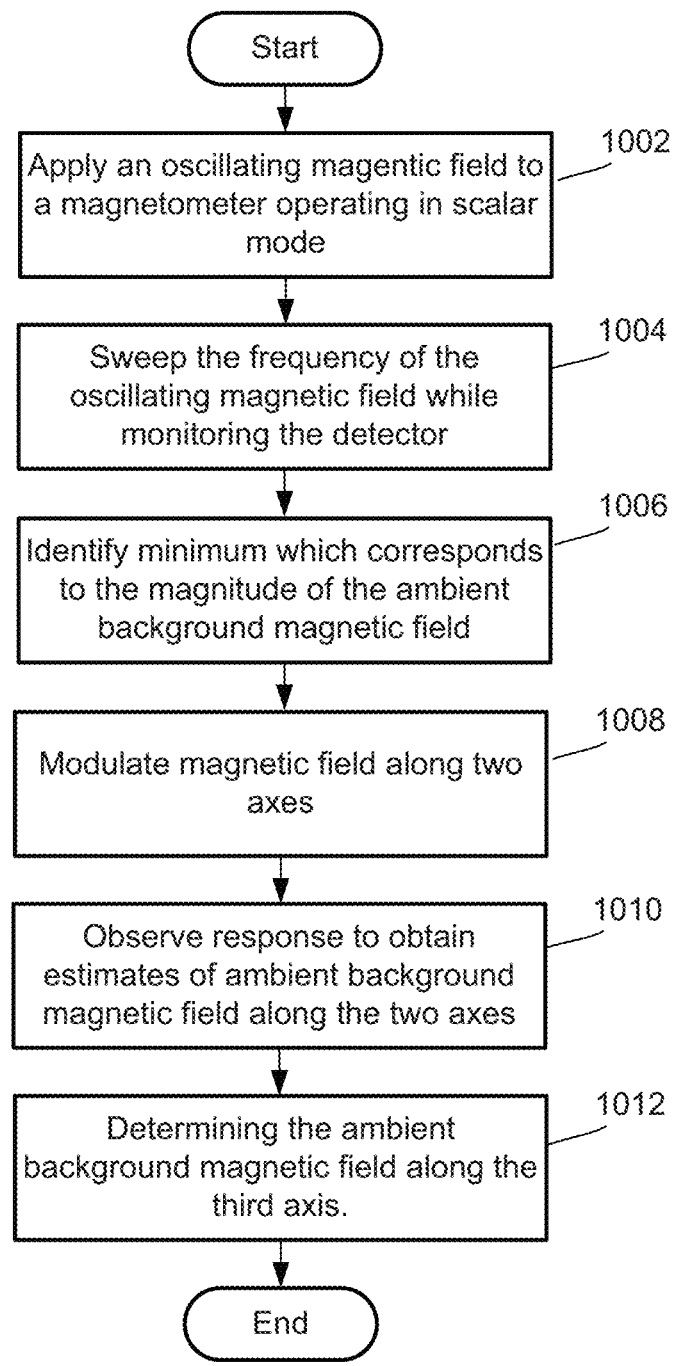
FIG. 10 is a flowchart of another embodiment of method of determining a compensation field, according to the invention.

FIG. 10 illustrates an embodiment of such a method which can, at least in some instances, be used for steps 402 and 404 in FIG. 4 or steps 502 and 504 in FIG. 5. First, a magnetometer operating in scalar mode is used to determine the magnitude |B| of the ambient background magnetic field. FIG. 9, described above, illustrates one arrangement for making such a measurement. The process can be thought of as using a driven oscillator for measuring the resonance frequency ft of the oscillator, also known as Larmor frequency, that is directly related to the magnitude of the magnetic field B by the gyromagnetic ratio γ of the atomic species used in the OPM according to Equation 2:

$$\omega_0 = \gamma |B| \qquad 2)$$

As an example, an OPM is placed inside a passive magnetic shield. The passive shield attenuates the ambient background magnetic field at the position of the OPM by a factor of, for example, 500 to 1000. Alternatively, similar measurements can be performed in an unshielded environment or in a partially shielded environment with shielding factors ranging from 10 to 500. In step 1002, to estimate |B| using the OPM the motion of the spins is driven using an oscillating magnetic field $B_{mod}(t)=B_m \cos(\omega_m t) \hat{x}$ where $\omega_m$ is generated using a local oscillator (for example, LO_x 982 of FIG. 9). In step 1004, the frequency $\omega_m$ is swept (using, for example, a linear chirp) while the absorption of the transmitted light is monitored by the detector. One example of the result is illustrated in the top graph in FIG. 11 which graphs the detector voltage versus the scan time. The bottom graph of FIG. 11 graphs the drive frequency versus the scan time. In general the oscillating field can be applied along any of the x, y, or z Cartesian axes or any combinations of axes. Alternatively, the motion of the spins can be driven by modulating the pumping rate caused by the pumping light source.

Figure 11:
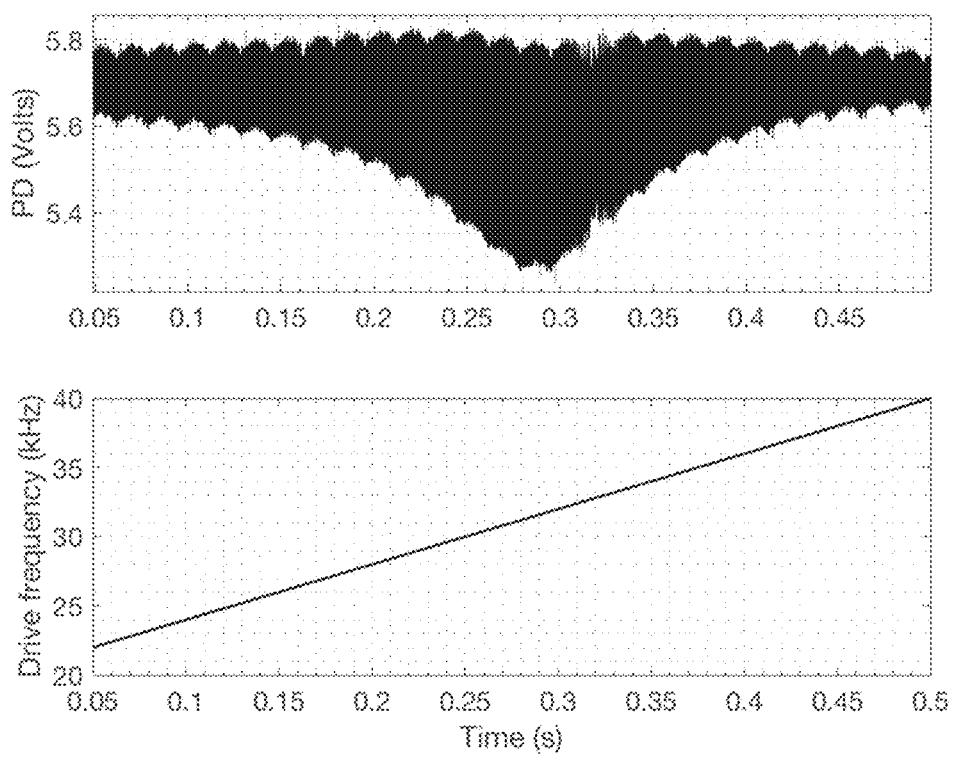
FIG. 11 illustrates a top graph of measured detector voltage versus time and a bottom graph of drive frequency versus time, according to the invention.

In step 1006, a minimum or dip (or maximum/peak depending on the orientation of the oscillating field with respect the light propagation axis) is observed when $\omega_m$ is close to the Larmor frequency $\omega_0$ of the alkali metal atoms in the vapor cell, as illustrated in FIG. 11. The specific example of FIG. 11 shows a dip at about 31038 Hz, corresponding to a magnetic field with |B|=4434 nT.

Figure 12:
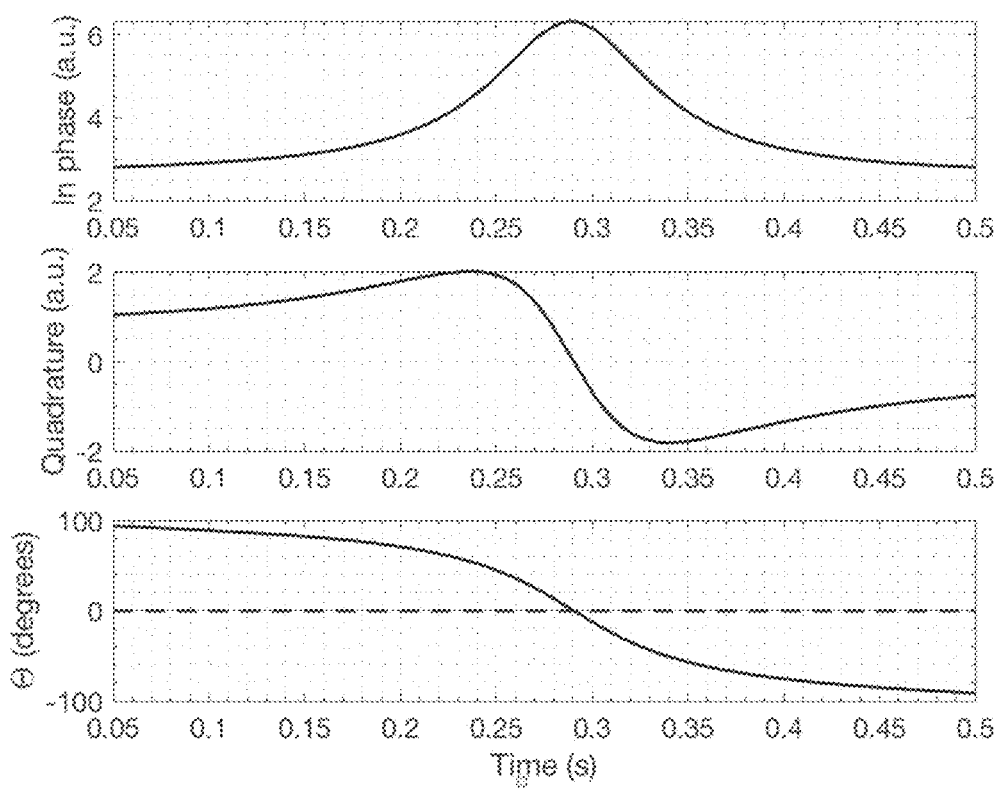
FIG. 12 illustrates graphs of in-phase ("U"), quadrature ("V"), and phase angle ("θ") outputs of a lock-in amplifier during sweeping of a frequency of an applied magnetic field, according to the invention.

Alternatively or additionally, to determine the resonance frequency with higher precision a lock-in amplifier (LIA), as shown in FIG. 9, can be used. FIG. 12 illustrates the outputs (U: in-phase, V: quadrature, and phase) where the frequency reference of the amplifier is the first harmonic of the LO_x. In the illustrated embodiment, the phase is related to the mismatch between the frequency $\omega_m$ of LO_x and the Larmor frequency $\omega_0$ and magnetic resonance linewidth ΔB by Equation 3.

$$\Theta = \arctan\left(\frac{\omega_m - \omega_0}{\gamma \Delta B}\right) \qquad 3)$$

In the regime arctan $$\left(\frac{\omega_m - \omega_0}{\gamma \Delta B}\right) \approx \left(\frac{\omega_m - \omega_0}{\gamma \Delta B}\right)$$

the phase Θ, and knowledge of $\omega_m$ and ΔB, can then be used to determine wo which, using Equation 2, provides an estimate of |B|.

Once the absolute value of the B-field has been estimated, the vector components, $B_x$, $B_y$, and $B_z$, of the ambient background magnetic field can be estimated using a magnetometer operating in the non-SERF vector mode. Oscillatory fields, $B_i(t)=\beta_i \cos(\omega_i t) \hat{i}$, can be used along axes i=x, y, z, with amplitude $\beta_I$ and frequency $\omega_i$. Consider the oscillatory field along the z axis: $B_z(t)=\beta_z \cos(\omega_z t) \hat{z}$.

From Equation 2, $$\omega_0 = \gamma |B| = \gamma \sqrt{B_x^2 + B_y^2 + B_z^2 + 2B_z\beta_z\cos(\omega_z t) + (\beta_z\cos(\omega_z t))^2}$$

Using $|B_0|$ to denote $$|B_0| = \sqrt{B_x^2 + B_y^2 + B_z^2} \quad \text{and}$$

assuming $$\frac{\beta_z}{|B_0|} \ll 1,$$

to first order the phase of the LIA output (see Equation 3) contains an oscillating component at the first harmonic of $\omega_z$ whose amplitude is related to $$B_z: \Theta \approx \frac{\beta_z}{|B_0|\Delta B} B_z \cos(\omega_z t)$$

assuming $\omega_m = \gamma |B_0|$.

In the general case, $$\Theta \approx \frac{\beta_z}{|B_0|\Delta B} B_z \cos(\omega_z t) + \frac{\beta_x}{|B_0|\Delta B} B_x \cos(\omega_x t) + \frac{\beta_y}{|B_0|\Delta B} B_y \cos(\omega_y t)$$

Figure 13:
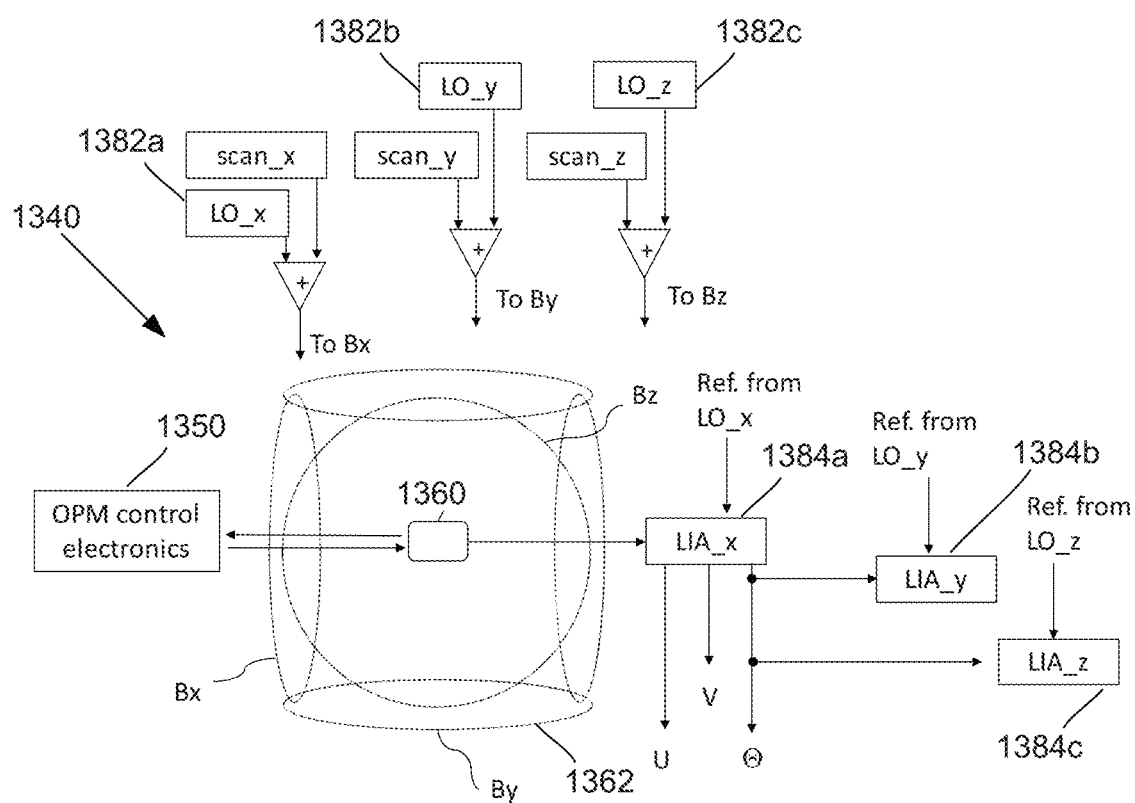
FIG. 13 is a schematic view of one embodiment of an arrangement of a magnetometer, magnetic field generators, three local oscillators, and three lock-in amplifiers, according to the invention.

Thus, to obtain each of the cartesian components $B_x$, $B_y$, $B_z$ of the ambient background magnetic field three different lock-in-amplifiers can be used with each referenced to the appropriate frequency $\omega_x$, $\omega_y$, $\omega_z$, respectively, as illustrated in FIG. 13. FIG. 13 illustrates one embodiment of a portion of a magnetic field measurement system 1340 with a computing device 1350 (designated as the "OPM control electronics"), a magnetometer 1360, and a magnetic field generator 1362 disposed around the magnetometer. The magnetic field generator 1362 includes three pairs of coils (labeled Bx, By, and Bz) and arranged to produce three fields $B_x$, $B_y$, and $B_z$. The embodiment illustrated in FIG. 13 has three local oscillators (LO_x, LO_y, LO_z) 1382a, 1382b, 1382c applied to the coils Bx, By, Bz, respectively, so that the coils can generate an RF field with a frequency $\omega_x$, $\omega_y$, $\omega_z$, respectively, that can be swept. The embodiment illustrated in FIG. 13 also includes three lock-in amplifiers (LIA_x, LIA_y, LIA_z) 1384a, 1384b, 1384c that each receive input from the detector of the magnetometer 1360 and the respective local oscillator 1382a, 1382b, 1382c and can be used to provide in-phase ("U"), quadrature ("V"), and phase angle ("$\Theta$") outputs based on the inputs.

For instance, to retrieve $B_z$, LIA_z in FIG. 13 produces in-phase output given by $V_{LIABz}$ $$V_{LIABz} \approx \frac{\beta_z}{|B_0|\Delta B} B_z \quad 4)$$

From Equation 4 and calibration of the ratio $$\frac{\beta_z}{|B_0|},$$

$B_z$ can be estimated from the phase output of LIA_z.

In step 1008, the magnetic field is modulated along two of the axes and, in step 1010, the response to the modulation is observed to obtain estimates of the ambient background magnetic field along the two axes. In step 1012, measurement the third vector component, Bx in this case, can be achieved by introducing a third oscillating field along the x axis.

In at least some embodiments, the resolution in the measurement of a vector component of the magnetic field is limited by the intrinsic sensitivity (spectral density) of the scalar OPM, $\delta B_s$, and the ratio $$\frac{\beta_v}{|B_0|},$$

thus the resolution $\delta B_v$ of the measurement of a vector component of the field B in a bandwidth $BW_s$ is equal to $$\Delta B_v = \delta B_s \sqrt{BW_s} \times \frac{|B_0|}{\beta_v}.$$

As indicated in steps 506 and 508 in FIG. 5, the compensation field can be updated by measuring the reduced ambient background magnetic field using a SERF mode OPM. These steps can be utilized in conjunction with the methods illustrated in FIGS. 8 and 10. As an example, the magnetic field generators can apply magnetic field components Bx', By', Bz', as determined using the method in any one of FIG. 4, 5, 8, or 10. Then a sinusoidal field is applied along y and z, to retrieve, using the SERF mode OPM, the residual vector components of the reduced ambient background magnetic field which, in at least some embodiments, is at a resolution beyond $\Delta B_v$. The compensation field can then be updated to B'=x*(Bx'+$\Delta$Bx')+y*(By'+$\Delta$By')+z*(Bz'+$\Delta$Bz').

A magnetic field measurement system may include an array of magnetometers with each magnetometer (or each set or pair of magnetometers) separately operating according to any one of the methods illustrated in FIG. 4, 5, 8 or 10 or any similar method. Such an array allows for the detection of neural signals (or other signals of interest) over a region, such as the head of a user in the case of MEG. Each magnetometer (or each set or pair of magnetometers) may operate individually or may information regarding the ambient background magnetic field may be shared for use with multiple magnetometers (or sets or pairs of magnetometers).

In at least some embodiments, a combined i) SERF mode and ii) scalar or non-SERF vector mode magnetometer in a single device can provide high sensitivity, high dynamic range when combined with active shielding. In at least some embodiments, a SERF mode magnetometer and scalar or vector mode magnetometer utilizing the same vapor cell can provide similar results. In other embodiments, the two magnetometers are separate from each other, but are preferably located close together. In at least some embodiments, a combined i) SERF mode and ii) scalar or non-SERF vector mode magnetometer can be used with auxiliary sensors. Some embodiments may also include passive shielding or partial passive shielding and or flux concentrators as described in U.S. Provisional Patent Application No. 62/719,928, incorporated herein by reference in its entirety.

In at least some embodiments, the system allows the magnetic compensation field to match exactly (within the sensitivity of the scalar or non-SERF vector mode magnetometer) to the field at the vapor cell. In at least some embodiments, the system allows for a very small device compared to using another high-dynamic range method. In at least some embodiments, the system allows for very fast and accurate finite-field measurements compared to using another high-bandwidth magnetometer. In at least some embodiments, the system can be realized as a magnetometer or gradiometer or both. In at least some embodiments, the system when combined with auxiliary sensors allows for fast and accurate measurements.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification provides a description of the invention and its manufacture and use. Since many embodiments of the invention can be made without departing from the spirit and scope of the invention, the invention also resides in the claims hereinafter appended.

What is claimed as new and desired to be protected by Letters Patent of the United States is:

1. A magnetic field measurement system, comprising:
   at least two magnetometers, wherein the at least two magnetometers comprise a first magnetometer configured to operate in a first mode selected from a scalar mode or a vector mode and a second magnetometer configured to operate in a spin exchange relaxation free (SERF) mode which is different from the first mode;
   at least one magnetic field generator;
   a processor coupled to the at least two magnetometers and the at least one magnetic field generator and configured to:
     i) measure an ambient background magnetic field using the first magnetometer in the first mode;
     ii) generate, in response to the measurement of the ambient background magnetic field, a compensation field using the at least one magnetic field generator;
     iii) measure a target magnetic field using the second magnetometer in the SERF mode; and
     iv) determine when the second magnetometer is not operating in the SERF mode and automatically perform steps i) and ii) again.

2. The magnetic field measurement system of claim 1, wherein each of the at least two magnetometers comprises a vapor cell and the first and second magnetometers share the same vapor cell.

3. The magnetic field measurement system of claim 1, wherein the processor is further configured to:
   measure the ambient background magnetic field, reduced by the compensation field, using the second magnetometer in the SERF mode; and
   update, in response to the measurement of the ambient background magnetic field reduced by the compensation field, the compensation field using the at least one magnetic field generator.

4. The magnetic field measurement system of claim 1, wherein measuring the ambient background magnetic field comprises, for each of two or three orthogonal axes:
   applying a first magnetic field along the axis;
   sweeping a frequency of the first magnetic field;
   measuring responses by the first magnetometer in the first mode during the sweeping; and
   determining a vector component of the ambient background magnetic field along the axis by observing a maximum or minimum in the responses or fitting the responses to a Lorentzian function.

5. The magnetic field measurement system of claim 1, wherein measuring the ambient background magnetic field comprises:
   applying a first magnetic field along a first axis;
   sweeping a frequency of the first magnetic field;
   measuring responses by the first magnetometer in the first mode during the sweeping; and
   determining a magnitude of the ambient background magnetic field along the first axis by observing a maximum or minimum in the responses or fitting the responses to a Lorentzian function.

6. The magnetic field measurement system of claim 1, further comprising
   at least one local oscillator coupled to the at least one magnetic field generator; and
   at least one lock-in amplifier, each of the at least one lock-in amplifier coupled to a one of the at least one local oscillator and at least one of the at least two magnetometers.

7. The magnetic field measurement system of claim 1, wherein the processor is further configured to repeat steps i) and ii) periodically at a selected repetition rate.

8. The magnetic field measurement system of claim 1, wherein the processor is further configured to repeat steps i) and ii) aperiodically.

9. A magnetic field measurement system, comprising:
   at least one magnetometer;
   at least one magnetic field generator;
   a processor coupled to the at least one magnetometer and the at least one magnetic field generator and configured to:
     i) measure an ambient background magnetic field using at least one of the at least one magnetometer in a first mode selected from a scalar mode or a vector mode;
     ii) generate, in response to the measurement of the ambient background magnetic field, a compensation field using the at least one magnetic field generator;
     iii) measure a target magnetic field using at least one of the at least one magnetometer in a spin exchange relaxation free (SERF) mode which is different from the first mode; and
     iv) determine when the at least one of the at least one magnetometer is not operating in SERF mode and automatically perform steps i) and ii) again,
   wherein measuring the ambient background magnetic field comprises
   applying a first magnetic field along a first axis;
   sweeping a frequency of the first magnetic field;
   measuring responses by the at least one of the at least one magnetometer in the first mode during the sweeping; and
   determining a magnitude of the ambient background magnetic field along the first axis by observing a maximum or minimum in the responses or fitting the responses to a Lorentzian function, and
   for each of two orthogonal axes, orthogonal to the first axis:
     applying a second magnetic field along the orthogonal axis;
     modulating the second magnetic field;

measuring responses by the at least one of the at least one magnetometer in the vector mode during the modulation; and determining a vector component of the ambient background magnetic field along the orthogonal axis by observing the responses to the modulated second magnetic field.

10. A method of operating the magnetic field measurement system of claim 1, the method comprising:

i) measuring the ambient background magnetic field using the first magnetometer operating in the first mode;

ii) generating, in response to the measurement of the ambient background magnetic field, the compensation field using the at least one magnetic field generator; and iii) measuring the target magnetic field using the second magnetometer operating in the SERF mode; and iv) determining when the second magnetometer is not operating in SERF mode and performing steps i) and ii) again.

11. The method of claim 10, each of the at least two magnetometers comprises a vapor cell and the first and second magnetometers share the same vapor cell.

12. The method of claim 10, further comprising:

measuring the ambient background magnetic field, reduced by the compensation field, using the second magnetometer in the SERF mode; and updating, in response to the measurement of the ambient background magnetic field reduced by the compensation field, the compensation field using the at least one magnetic field generator.

13. The method of claim 10, wherein measuring the ambient background magnetic field comprises, for each of two or three orthogonal axes:

applying a first magnetic field along the axis;
sweeping a frequency of the first magnetic field;
measuring responses by the first magnetometer in the first mode during the sweeping; and
determining a vector component of the ambient background magnetic field along the axis by observing a maximum or minimum in the responses or fitting the responses to a Lorentzian function.

14. The method of claim 10, wherein measuring the ambient background magnetic field comprises:

applying a first magnetic field along a first axis;
sweeping a frequency of the first magnetic field;
measuring responses by the first magnetometer in the first mode during the sweeping; and
determining a magnitude of the ambient background magnetic field along the first axis by observing a maximum or minimum in the responses or fitting the responses to a Lorentzian function.

15. The method of claim 14, wherein measuring the ambient background magnetic field further comprises, for each of two or three orthogonal axes:

applying a first magnetic field along the axis;
modulating the first magnetic field;
measuring responses by the first magnetometer in the vector mode during the modulation; and
determining a vector component of the ambient background magnetic field along the axis by observing the responses to the modulated first magnetic field.

16. A magnetic field measurement system, comprising:

at least one magnetometer, wherein the at least one magnetometer comprises a) at least one first magnetometer configured for operation in a first mode selected from a scalar mode or a vector mode and b) at least one second magnetometer configured for operation in a spin exchange relaxation free (SERF) mode which is different from the first mode;

at least one magnetic field generator;

a processor coupled to the at least one magnetometer and the at least one magnetic field generator and configured to:

i) measure an ambient background magnetic field using at least one of the at least one first magnetometer in the first mode;

ii) generate, in response to the measurement of the ambient background magnetic field, a compensation field using the at least one magnetic field generator;

iii) measure a target magnetic field using at least one of the at least one second magnetometer in the SERF mode;

iv) determine when the at least one of the at least one second magnetometer is not operating in the SERF mode and automatically perform steps i) and ii) again; and v) repeat steps i) and ii) aperiodically.

17. The magnetic field measurement system of claim 16, wherein each of the at least one first magnetometer and each of the at least one second magnetometer comprises a vapor cell and at least one of the at least one first magnetometer and at least one of the at least one second magnetometers share the same vapor cell.

18. The magnetic field measurement system of claim 16, wherein the processor is further configured to:

measure the ambient background magnetic field, reduced by the compensation field, using at least one of the at least one second magnetometer; and update, in response to the measurement of the ambient background magnetic field reduced by the compensation field, the compensation field using the at least one magnetic field generator.

19. The magnetic field measurement system of claim 16, wherein measuring the ambient background magnetic field comprises, for each of two or three orthogonal axes:

applying a first magnetic field along the axis;
sweeping a frequency of the first magnetic field;
measuring responses by the at least one of the at least one first magnetometer in the first mode during the sweeping; and
determining a vector component of the ambient background magnetic field along the axis by observing a maximum or minimum in the responses or fitting the responses to a Lorentzian function.

20. The magnetic field measurement system of claim 16, wherein measuring the ambient background magnetic field comprises:

applying a first magnetic field along a first axis;
sweeping a frequency of the first magnetic field;
measuring responses by the at least one of the at least one first magnetometer in the first mode during the sweeping; and
determining a magnitude of the ambient background magnetic field along the first axis by observing a maximum or minimum in the responses or fitting the responses to a Lorentzian function.

21. The magnetic field measurement system of claim 20, wherein measuring the ambient background magnetic field further comprises, for each of two or three orthogonal axes:

applying a first magnetic field along the axis;
modulating the first magnetic field;
measuring responses by the at least one of the at least one first magnetometer in the vector mode during the modulation; and determining a vector component of the ambient background magnetic field along the axis by observing the responses to the modulated first magnetic field.

22. The magnetic field measurement system of claim 16, further comprising
at least one local oscillator coupled to at least one of the at least one magnetic field generator; and
at least one lock-in amplifier, each of the at least one lock-in amplifier coupled to a one of the at least one local oscillator and at least one of the at least one first magnetometer.

23. A magnetic field measurement system, comprising:
at least one magnetometer;
at least one magnetic field generator;
a processor coupled to the at least one magnetometer and the at least one magnetic field generator and configured to:
  i) measure an ambient background magnetic field using at least one of the at least one magnetometer in a first mode selected from a scalar mode or a vector mode;
  ii) generate, in response the measurement of the ambient background magnetic field, a compensation field using the at least one magnetic field generator;
  iii) measure a target magnetic field using at least one of the at least one magnetometer in a spin exchange relaxation free (SERF) mode which is different from the first mode;
  iv) determine when the at least one of the at least one magnetometer is not operating in the SERF mode and automatically perform steps i) and ii) again; and
  v) repeat steps i) and ii) aperiodically.

24. The magnetic field measurement system of claim 23, wherein the at least one magnetometer comprises a first magnetometer configured to operate in both the first mode and the SERF mode and the processor is configured to operate the first magnetometer in both the first mode and the SERF mode.

25. The magnetic field measurement system of claim 23, wherein the at least one magnetometer comprises a first magnetometer configured to operate in the first mode and a second magnetometer configured to operate in the SERF mode.

* * * * *